(12) United States Patent
Pfenniger et al.

(10) Patent No.: US 8,051,520 B2
(45) Date of Patent: *Nov. 8, 2011

(54) TOOTHBRUSH AND PROCESS FOR PRODUCING THE SAME

(75) Inventors: Philipp Pfenniger, Triengen (CH); Adrian Pfenniger, Triengen (CH); Franz Fischer, Triengen (CH)

(73) Assignee: Trisa Holding AG, Triengen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/656,979

(22) Filed: Feb. 22, 2010

(65) Prior Publication Data

US 2010/0154152 A1   Jun. 24, 2010

Related U.S. Application Data

(60) Continuation of application No. 12/213,075, filed on Jun. 13, 2008, now abandoned, which is a division of application No. 11/369,965, filed on Mar. 8, 2006, now Pat. No. 7,721,371, which is a continuation of application No. PCT/EP2004/012708, filed on Nov. 10, 2004.

(30) Foreign Application Priority Data

Nov. 13, 2003 (EP) ..................... 03025936

(51) Int. Cl.
   *A61C 17/22* (2006.01)
(52) U.S. Cl. .......................... 15/22.1; 15/21.1
(58) Field of Classification Search ............ 15/22.1, 15/21.1, 22.2, 23, 167.1, 143.1; 30/34.2, 30/44; 200/276, 276.1, 302.2

See application file for complete search history.

(56) References Cited

U.S. PATENT DOCUMENTS

| | | | |
|---|---|---|---|
| 3,274,631 A | 9/1966 | Spohr | |
| 3,370,214 A | 2/1968 | Robert | |
| 3,371,260 A | 2/1968 | Jackson et al. | |
| 3,463,994 A | 8/1969 | Sphor | |
| 3,577,579 A | 5/1971 | Duve | |
| 4,275,749 A | 6/1981 | Caroli | |
| 4,827,552 A | 5/1989 | Bojar et al. | |
| 5,261,430 A | 11/1993 | Mochel | |
| 5,572,762 A | 11/1996 | Scheiner | |
| 5,998,945 A | 12/1999 | Carlucci | |
| 6,199,239 B1 | 3/2001 | Dickerson | |
| 6,237,178 B1 | 5/2001 | Krammer et al. | |
| 6,326,097 B1 | 12/2001 | Hockaday | |

(Continued)

FOREIGN PATENT DOCUMENTS

| | | | |
|---|---|---|---|
| CH | 656 987 A5 | 12/1978 | |
| DE | 29 16 215 A | 10/1980 | |
| DE | 195 13 539 A1 | 10/1996 | |

(Continued)

*Primary Examiner* — Shay Karls

(74) *Attorney, Agent, or Firm* — Oliff & Berridge, PLC

(57) ABSTRACT

The invention relates to an electric toothbrush (10) having a rechargeable energy store (24) that is arranged in an inner space (36) in the body (12) of the toothbrush (10). The inner space (36) is sealed by a primary sealing element (56) against splash water and other detrimental influences. At least one contact element (28) for an external power supply unit (46) produces an electrically conductive connection to the energy store (24). The contact element is located either within the inner space (36), it being possible for the primary sealing element (56) to be removed for charging purposes, or outside the inner space (36), in which case it is optionally protected by an additional secondary sealing element (76). The invention also relates to a process for producing such a toothbrush.

44 Claims, 16 Drawing Sheets

U.S. PATENT DOCUMENTS

| | | |
|---|---|---|
| 6,513,947 B1 | 2/2003 | Huang |
| 6,920,659 B2 | 7/2005 | Cacka et al. |
| 7,028,405 B2 | 4/2006 | Paas et al. |
| 2002/0119697 A1* | 8/2002 | Chan .............................. 439/519 |
| 2003/0037391 A1 | 2/2003 | Pfenniger et al. |
| 2003/0098669 A1 | 5/2003 | Hensel |
| 2003/0204924 A1 | 11/2003 | Grez et al. |
| 2004/0060138 A1 | 4/2004 | Pfenniger et al. |
| 2004/0168270 A1 | 9/2004 | Choi et al. |
| 2005/0022322 A1 | 2/2005 | Spohr |

FOREIGN PATENT DOCUMENTS

| | | |
|---|---|---|
| DE | 199 05 551 A1 | 6/2000 |
| GB | 2 094 574 A | 9/1982 |
| GB | 2 278 537 A | 12/1994 |
| JP | A 07-263032 | 10/1995 |
| WO | WO 97/04719 A | 2/1997 |
| WO | WO 01/58306 A1 | 8/2001 |
| WO | WO 03/024353 A1 | 3/2003 |
| WO | WO 03/069761 A1 | 8/2003 |

* cited by examiner

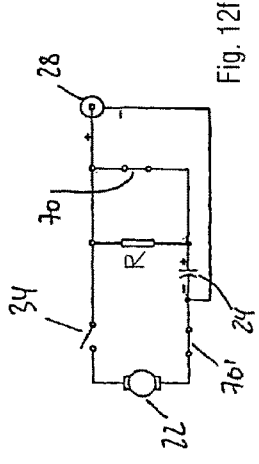
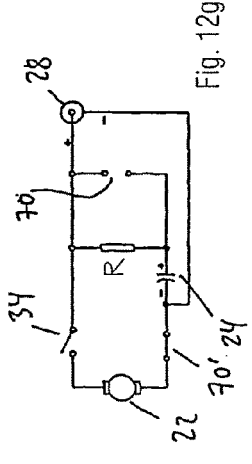
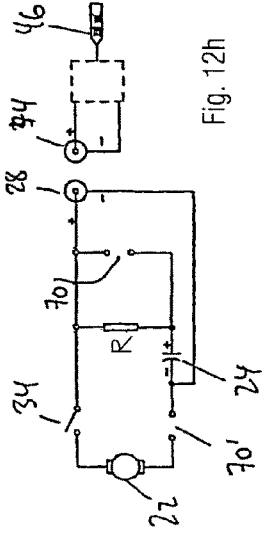
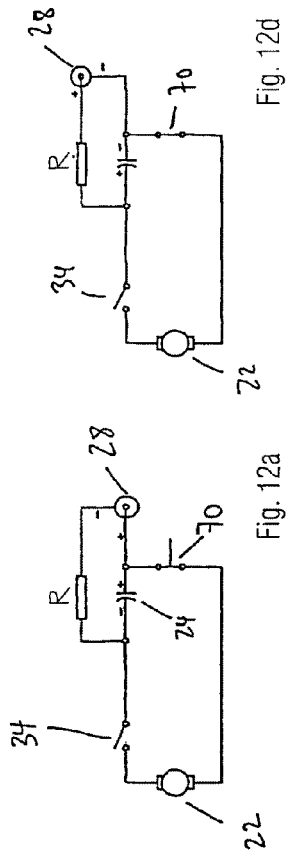
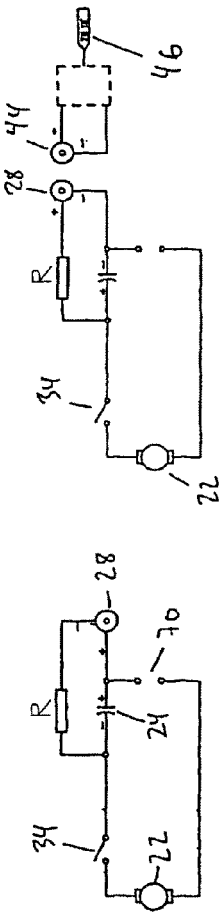
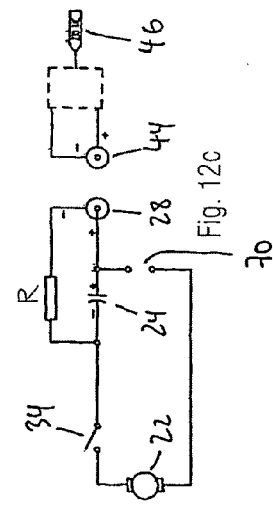

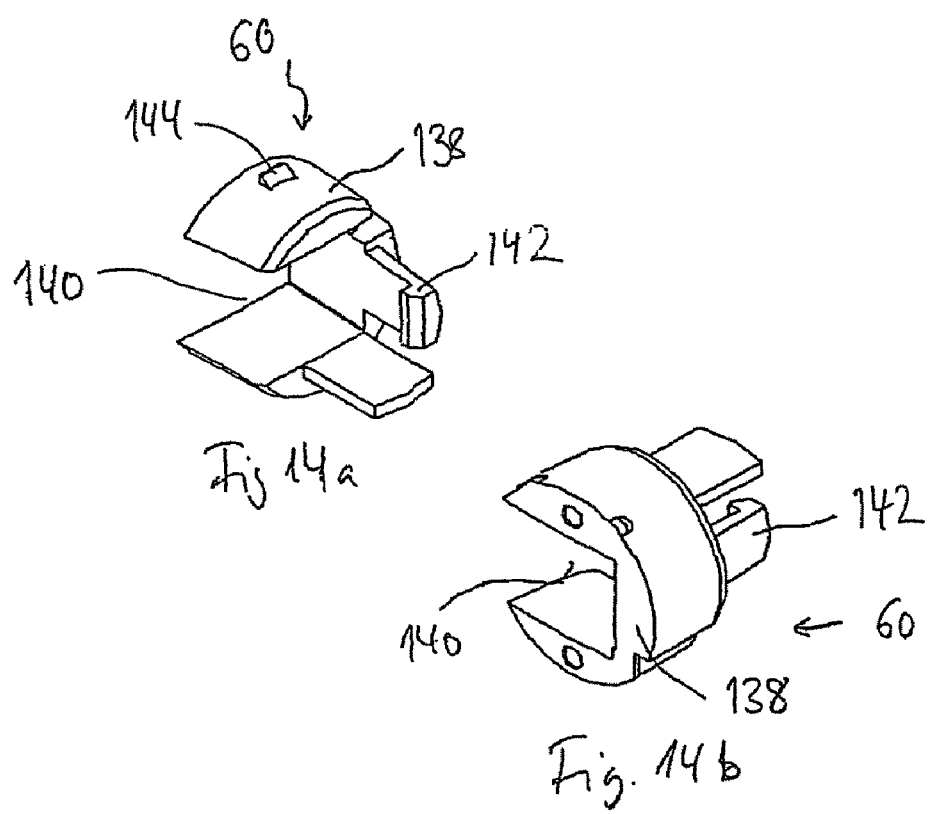

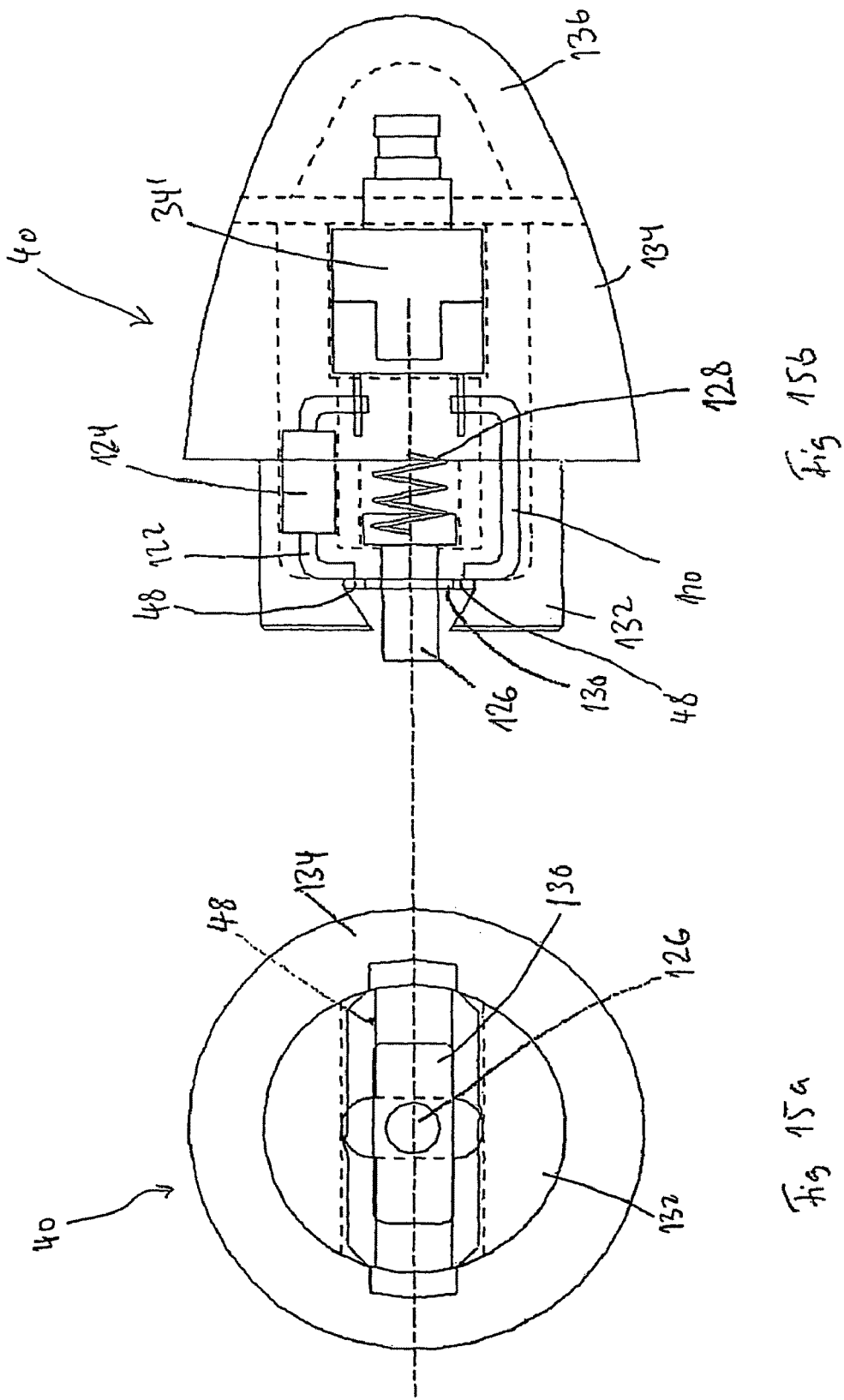

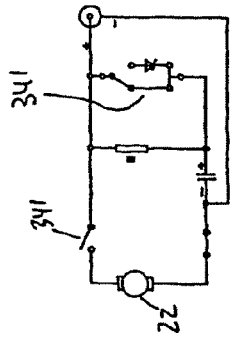
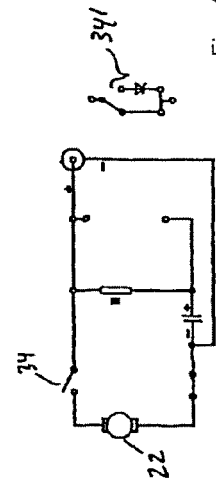
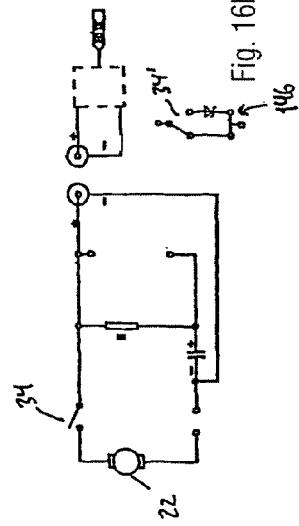
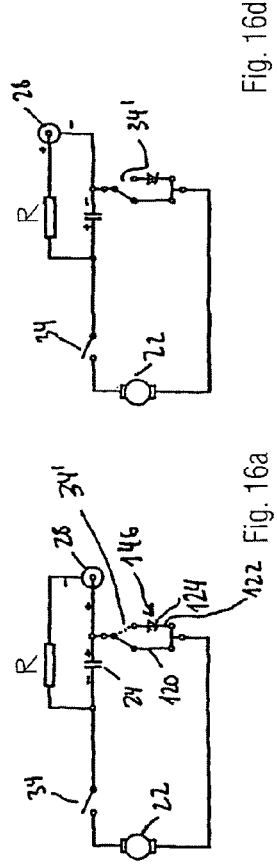
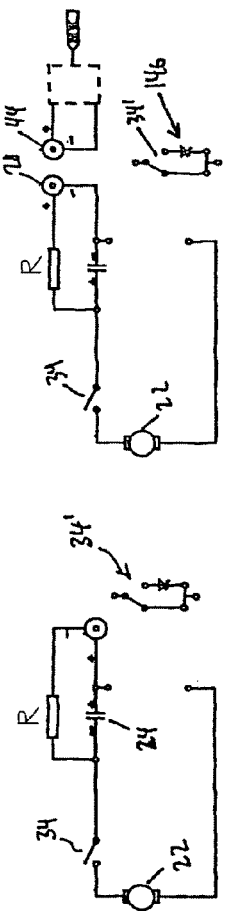
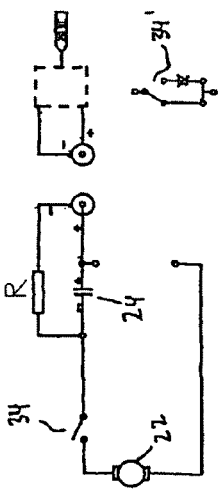

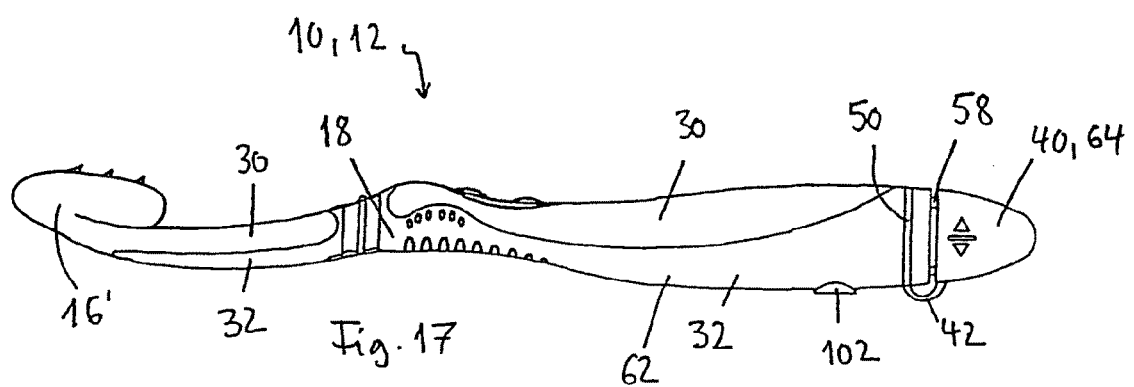

TOOTHBRUSH AND PROCESS FOR PRODUCING THE SAME

CROSS-REFERENCE TO RELATED APPLICATIONS

This is a Continuation of application Ser. No. 12/213,075 filed Jun. 13, 2008, which is a Division of application Ser. No. 11/369,965 filed Mar. 8, 2006, which is a Continuation of International Application No. PCT/EP2004/012708 filed Nov. 10, 2004, which claims the benefit of European Patent Application No. 03025936.0 filed Nov. 13, 2003. The entire disclosure of the prior applications is hereby incorporated by reference herein in its entirety.

BACKGROUND

This invention relates to a toothbrush having an electrically operated functional unit and to a process for producing such a toothbrush.

Electric toothbrushes with rechargeable energy stores (storage batteries) are known and widely available on the market. In most cases, electrical energy is transmitted inductively to the energy store from the charging station. This is described, for example, in CH 656 987. Since there is no need for any electrical line connections between the energy store and the charging station, the advantage of this charging method resides in the straightforward handling for the user (i.e. straightforward positioning in the charging station without trying to find contact) and in the low level of susceptibility to external influences, e.g. water or toothpaste, which may result in contamination or corrosion of electrical contacts. The disadvantage with inductive charging resides in the high production costs and in the large amount of space required for the charging station, which comprises a high-outlay charging circuit. The toothbrushes are likewise large, heavy and unwieldy since, in addition to the storage batteries, at least one secondary coil with a rectifier arrangement has to be present.

U.S. Pat. No. 4,827,552 discloses an electric toothbrush of the generic type having an energy store which can be charged up via a plug-in contact. The contact element is located without protection at the foot of the electric toothbrush and thus in a region in which water dripping off from the brush head accumulates. Satisfactory current transmission is put at risk by corrosion and contamination of the contact elements.

SUMMARY

The object of the invention is to develop a cost-effective charging method which allows reliable operation, can be used in a space-saving manner, is as straightforward as possible to implement and allows minimal dimensions of the electric toothbrush.

The direct loading method for electrical equipment, e.g. mobile telephones, which is known per se is adapted according to the invention such that it can also be used for toothbrushes having electrical functional components in the wet region. The charging current is transmitted to the electric toothbrush directly, i.e. by means of contact elements, using a power supply unit—comprising a transformer and rectifying element or comprising a clocked electronic circuit. Provided within the toothbrush, instead of a costly charging circuit which takes up a lot of space, is just one contact element, if appropriate with connecting lines to the storage battery. The toothbrush may thus be configured to be considerably more slender and lightweight than conventional electric toothbrushes with inductive charging and is easier to handle. For the purpose of fulfilling aesthetic requirements, there is more design freedom. The invention makes it possible to use favorable, mass-produced components, possibly standard elements, and thus power supply units which are already present in the home.

According to the invention, the inner space of the toothbrush, in which the energy store is located, is sealed by a primary sealing element, with the result that it is not possible for any water or other foreign matter to penetrate during intended use of the toothbrush. This prevents corrosion and contamination of the energy store and of the electrical contacts.

In the case of one variant of the invention, the energy store and contact elements are both located in the inner space, which is sealed by the primary sealing element during intended use, i.e. during teeth cleaning. The primary sealing element may be moved at least to the extent where the contact element is accessible for the charging operation.

In the case of another variant of the invention, the inner space is permanently sealed, i.e. the inner space is closed in a water-tight manner during intended use of the toothbrush and during the charging operation. Provision may be made for it to be possible for the primary sealing element to be removed, for example for repair work. It is also possible, however, for the energy store to be fully set in place by injection molding. The contact element is located outside the inner space and is optionally sealed by a secondary sealing element, e.g. a closure cap.

If just the inner space is permanently sealed, the contact element is arranged, for example, on the surface of the handle region and/or of the neck region, in the region of the rear side and/or of the side regions. It may also be offset inward in relation to the surface and arranged in a cutout. It is thus positioned such that when the toothbrush is set down, this usually taking place with the toothbrush upright or with the front side located in the upward direction, it is not possible for any residues to form on the contact element by droplets of water and toothpaste flowing off. The opening of the contact elements, in the respective position, is provided on the side which is directed away from the direction in which the water flows. For producing one or more defined set-down positions, the electric toothbrush is preferably provided on the outer casing with geometrical elements (supporting protuberances) which are preferably formed from a soft component.

In an advantageous development in particular of the first variant of the invention, the charging logic is configured such that operation of the appliance during charging is not possible. This prevents short-circuits and contamination of the inner space and increases user safety.

The toothbrush is preferably packaged such that its presentation in the packaging is self-explanatory. For example, the power supply unit and/or the contact elements are/is visible through viewing windows. In this way, it is also possible for the purchaser to check whether he/she already has a suitable power supply unit.

The functional component of the electric toothbrushes comprises, for example, a vibration element, which causes the head to vibrate, or a drive, by means of which the head part can be oscillated. It is also possible to provide other consumers, e.g. light, music, timing. Also preferably provided are switching elements which switch the energy consumers on or off in relation to the storage battery. Mechanical or electronic switches may be provided here. The switch can be triggered by the user (e.g. push button, rotary switch, butterfly, contact element in the closure, movement sensor, pressure sensor, etc.) or by other external influences. The storage battery is preferably of the NiCd (nickel cadmium) or NiMh (nickel metal hydride) type. Mass-produced AA or AAA cells are used. The appliances are preferably operated with a voltage of less than 4 volts, preferably at 1.2 volts. For cost-related reasons, a single 1.2 volt storage-battery cell should be used. An optimum duration of use per discharging cycle of the storage battery is at least 2 h, but preferably at least 5 h or more. If this can be achieved using a AAA cell, this size is preferred for space-related reasons. In the case of a toothbrush with a vibrating head part, the preferred capacity of cell AAA is 300-800 mAh; in the case of a toothbrush with a rotating head part, the preferred capacity of cell AA is 600-2300 mAh.

Since the storage battery can produce explosive gases such as oxygen and/or hydrogen particularly during the charging operation, the inner space is preferably sealed with a sealing element which is gas-permeable but protects the inner space against water. Use is preferably made of a corresponding membrane fitted on the hard component.

The electric toothbrush preferably consists of one or more structure-forming hard components (e.g. PS polystyrene, ABS acrylonitrile-butadiene-styrene, SAN styrene-acrylonitrile, PET polyester, PA polyamide) but preferably of PP polypropylene and at least one or more soft components. The soft components are preferably formed from thermoplastic elastomer TPE which has an affinity for the hard component used and is connected to the latter during two-component injection molding. The soft component is usually used for a flexible switching membrane. The electric toothbrush contains, inter alia, an inner space with electrical components which are closed off in a water-tight manner. The inner space is preferably formed by a core puller in the mold of the hard component and of the soft component.

A power supply unit is used in all the variants. This power supply unit is connected to the local power supply (e.g. 230 V AC or 115 V AC). The power supply unit is preferably designed such that the power plug is integrated in the housing and the power supply unit can thus be plugged directly into a socket. In this case, use is made of a class II power supply unit 4 kVolts and IP X4 (IEC Standard 60529, DIN 40050). In a less preferred variant, however, it is also possible to provide a power cable between the socket and power supply unit; in the case of this variant, it would be necessary to use a power supply unit with a higher degree of protection, e.g. IP X7. The power supply unit should always be kept short-circuit-proof.

In the power supply unit, the local AC supply voltage (e.g. 210-250 volts AC 50 Hertz) is transformed into a low DC voltage in order thus to charge up the storage battery. By means of a cable and contact element, then, the direct voltage (4-7 volts DC) is transmitted directly to the electric toothbrush from the power supply unit. The charging currents are preferably around 30-230 mA corresponding to 10% of the storage-battery capacity (C/10). This results in a charging period of 10-14 hours in the case of the abovementioned types of storage battery. The cable serves for bridging the distance between the next power-supply connection and a means for setting down the electric toothbrush. This cable length is between 0.5 m and 2 m, preferably 1.5 m. In a less preferred variant, the electric toothbrush is plugged directly into the power supply unit with corresponding contact elements.

Use is preferably made of contact elements of the plug and socket type. The plug is preferably fitted on the cable of the power supply unit. For safety reasons, use is made of a plug which has a hollow inner space and a phase provided on the outside and inside. This construction avoids short-circuits when the plug bears on an electrically conductive surface. The contact-connection element of the plug has approximately the following dimensions (length 3-15 mm, preferably 10 mm/diameter 2-10 mm, preferably 5.5 mm).

The contact element designed as a socket is preferably fitted in or on the electric toothbrush. It is preferably possible for the socket (e.g. by means of a pin) also to be contact-connected by other electrically conductive components (e.g. in the toothbrush cover) in addition to the plug. For this reason, this pin should have a minimum diameter of 1-4 mm, preferably 2.4 mm. The pin is preferably connected to the (+) terminal of the motor and of the storage battery. Preferably interacting with the contact element is a switch which, during the charging operation, disconnects the consumer and only charges the storage battery.

In order to keep the costs low, the plug-in contacts are preferably mass-produced parts. The metallic surfaces of the contact elements are usually surface-coated (e.g. gold, nickel, chromium, etc.). A layer of nickel guarantees good electrical conductivity D and particularly good corrosion resistance against the aggressive toothpaste/water mixture with low production costs. The dimensions of the socket are usually selected to be equal to or less than the diameter of the storage battery, with the result that the dimensions of the inner space can be minimized. (Outer dimensions: width/height of the socket using a size AAA storage battery preferably less than 10.5 mm, length dependent on the plug-in distance selected, size AA storage batteries less than 14.5 mm).

The plug-in operation is preferably carried out with a defined movement (translation, rotation or a combination thereof) of 1-10 mm and/or 10-180° preferably of the plug in relation to the socket. In the case of contamination and corrosion, this allows a certain amount of rubbing of the contact surfaces, which has a self-cleaning action and thus facilitates contact-connection. During the plug-in operation, a certain pressure is to be produced between the contact-connection surfaces (e.g. by means of spring action of one contact-connection surface on the other), and contamination can likewise be effectively scraped away as a result. The plug-in operation is thus preferably carried out by means of a combination of movement and pressure of the contact-connection surfaces in relation to one another. At the end of plug-in distance, the plug is intended to latch in the socket, this preventing independent release of the plug or loose contacts between the plug and socket. The force which is necessary for releasing the plug is preferably larger than the deadweight of the entire electric toothbrush in the pulling direction of the plug. The socket preferably undergoes form-fitting latching with its carrier unit, e.g. the printed circuit board, in order that the plug-in forces do not rest on the, for example, soldered electrical contacts.

Since certain forces are exerted in the above-defined plug-in operation, it should be ensured that fragile components of the electric toothbrush are not damaged. In particular, it should be ensured that the bristles are not crushed or flexible or vibration-damping means in the neck region are not deformed by the forces produced. For this reason, the contact elements are to be positioned on or in the handle such that the handle still has sufficient space available in order for it to be comfortably held in the other hand. In this respect, it is desirable for the contact elements to be positioned at one end of the handle or the other. In addition, the holding points in the handle region, at which the electric toothbrush should be held during the plug-in operation, are to be clearly marked for the user. For this purpose, use may be made of geometrical elements such as indents, protuberances, surface textures, etc., and/or zones with soft materials and/or a corresponding imprint.

The plug-in direction is proposed as an angle between −90° and 90° to the longitudinal axis of the handle part, although the plug-in operation preferably takes place in the direction of this main axis in order that the other hand can best be used, as has been explained above, for absorbing the plug-in forces.

The plug-in operation can be simplified by the contact elements having a rotationally symmetrical, preferably circular cross section. The relative positions of the plug-in contacts is thus not important and need not be sought by the user. It is only the plug-in direction which has to be correct. In the different variants, the plug-in direction is preferably provided parallel or perpendicularly to the opening direction of the closure.

The position of the contact elements in relation to the electric toothbrush is critical in respect of contamination tendency, sealing of the inner space, plug-in operation during charging and comfort during use of the electric toothbrush. In respect of the contamination, the contact element is to be positioned on the electric toothbrush such that, when the toothbrush is set down following the respective use, it is not possible for any residues of toothpaste to form on the contact element. The electric toothbrush is preferably provided with geometrical elements, preferably formed from soft components, on the outer casing in order that the set-down position, following use, is clearly defined for the user. In addition, the electrical contact elements should be provided at a location at which it is not possible for any droplets of water or toothpaste to be produced when the toothbrush is set down following use. In addition to one or, if need be, more defined horizontal set-down positions, the toothbrush glass or a flattened handle part, in the case of which the electric toothbrush assumes a more or less vertical position, should also be taken into consideration here. The opening of the contact elements (e.g. of the socket), in the respective position, is preferably provided on the side which is directed away from the direction in which the water flows.

A further criterion for the position of the contact elements is comfort during use. Since said contact elements comprise, at least in part, metallic components, the position is selected such that, during use of the electric toothbrush, the resulting cleaning pressure (approximately 100 g-1 kg; 300 g on average) cannot produce any impressions, as a result of the contact elements, on the hand guiding the toothbrush. In a variant, for this purpose, the contact elements are arranged on the toothbrush surface, in a slightly sunken manner therein, and are encased with, or embedded in, soft component, which performs a certain resilient action. The resulting flexible mounting allows easier plug-in and removal operations since the plug-in direction need not be maintained precisely. The contact element, in this case, can preferably be fitted laterally or on the rear side of the handle part. It is preferable, however, for the contact elements to be introduced in the inner space or in a border layer of the electric toothbrush and to be sealed by the primary sealing element, e.g. covered over by a protective plastic layer of soft or hard component or of a combination thereof. In the case of this variant, the surface of the handle part may be completely covered with plastics, so that it is not possible for any impressions to be produced during the cleaning operation. The contact elements are likewise better protected against contamination.

In respect of sealing of the inner space and of the contact elements, the following variants, which have already been mentioned above, apply:

(i) The contact elements are placed in the actual inner space of the electric toothbrush, at a location which is easily accessible for the user, preferably in the immediate vicinity of the separating line between the handle part and closure. The entire inner space including the contact element is closed off with sealing action by a primary sealing element, e.g. a closure. The primary sealing element can be produced in one operation with the electric toothbrush, from the same hard and soft component, possibly just from the soft component. A permanent connection, e.g. in the form of a film hinge, is optionally provided between the primary sealing element and the toothbrush handle. The contact elements are fixed on a solid carrier unit made of plastic or on a printed circuit board and are electrically connected to the storage batteries (e.g. by means of printed conductors or cables, etc.). This solid carrier unit may also contain further functional units such as switches, drive and storage battery, etc. It preferably comprises a printed circuit board with the contact elements firmly connected thereto, the storage battery and further circuit components, e.g. printed conductors, resistor. This so-called storage-battery subassembly is a self-contained system which has the outer appearance of a rechargeable battery with integrated plug-in contacts. This subassembly can be used like a conventional disposable battery. The terminals of the energy store are accessible from the outside directly or via the contact element.

In order to optimize the manageability of the electric toothbrush, it is proposed to place the contact elements in series with the storage battery (i.e. one behind the other) on the carrier unit. The diameter of the inner space thus corresponds approximately to the size of the storage battery plus carrier unit. In the variants in which a size AAA storage battery is used, the diameter of the AAA battery and the thickness of the carrier unit with printed circuit board and storage battery correspond approximately to the diameter of a AA battery. The minimal storage-battery subassembly described above may thus be replaced, with little outlay, by a AA battery. It is thus possible, with few changes (bridging the difference in length), to operate the electric toothbrush using a disposable AA battery. Furthermore, the same injection molds may be used for producing a rechargeable electric toothbrush and a toothbrush with a disposable energy store.

There is no risk, in the case of this variant, of the contact elements being contaminated, since the inner space is only opened for charging the storage battery. In this variant, it is preferably ensured that the appliance cannot be used when the inner space is open, e.g. during the charging operation, since the inner space, in this state, does not have a seal. In the case of this variant, the other technical components (such as drive, storage battery, etc.) are preferably covered by means of a shield which is not necessarily water-tight (e.g. with an installed plastic part or a self-adhesive plastic label). The shield gives protection, during the charging operation, against splash water in the wet cell and clearly shows the user the contact elements which are not covered thereby. Other technical units which could confuse the user are not visible. Preferably, the shield has latching-in means (e.g. snap-action lugs, projections) which allow the shield to be connected to the storage-battery subassembly. Further snap-action elements are optionally present on the shield, which secure the storage-battery subassembly radially with respect to the hard component of the toothbrush handle and hence prevent the storage-battery subassembly (with shield) from falling out.

(ii) The inner space of the electric toothbrush is sealed in relation to the contact elements by the primary sealing element. The contact elements themselves are not covered/sealed and can communicate freely with the exterior surroundings. In this variant, the contamination and corrosion tendency of the contact elements is greatest, but additional handling for the user, e.g. the removal of a closure or of a sealing element, is dispensed with. In order to ensure a satisfactory seal, the sealing element may be realized by a housing part with integrally molded or separate seals, e.g. O-rings. For production reasons, however, the contact elements are preferably placed in a form-fitting manner on the hard component and are then overmolded and/or encapsulated, and fixed, by means of the soft component and thus sealed from the inner space of the electric toothbrush. The contact elements communicate either directly or by means of an electrical connection, e.g. a plastic-sheathed stranded wire, with further electrical components, e.g. the printed circuit board or the storage battery, in the inner space of the toothbrush.

The variant (ii) may be extended by an additional secondary sealing element, which additionally seals the contact elements in relation to the exterior surroundings. All that is thus required for charging the appliance is to release the outer, secondary sealing element. The inner space is fully sealed in each state (during charging and during use). There is no provision made for the user to open the primary seal. In some circumstances, in the case of this variant, it is also possible for the electric toothbrushes to be used during the charging operation, i.e. with the contact element plugged in. The secondary seal may be produced in the form of an additional cover or of a flexibly deformable sealing lip. The secondary seal is also preferably produced with the soft component available. For cost-related reasons, secondary sealing elements should be produced in one operation with the hard or soft component provided. It is additionally proposed for these sealing elements to be firmly connected to the handle part of the electric toothbrush, e.g. by means of a film hinge or of a flexible connection made of elastomeric material. This prevents them from getting lost during the charging operation.

The storage-battery subassembly is required to comprise, at the minimum, a storage battery, resistor and carrier unit, e.g. in the form of a printed circuit board. If the contact element is not set in place in the body (closure, handle part) by injection molding, the contact element is also preferably a constituent part of the storage-battery subassembly, which can thus replace one or more disposable batteries. This subassembly, if necessary, may be supplemented by further components, e.g. by switching elements, timer function, motor, LED. The resistor used prevents the storage batteries from being overcharged and allows a constant charging current from the power supply unit. If use is made of a preferred power supply unit with an output power of, without load, 7 volts DC and, with load, 4 volts DC, at 230 mA, with different cell capacities, the following resistance values are achieved by way of example, depending on the variant:

| Cell capacity (mAh) | Charging current (mA) | Resistance (Ohm) |
|---|---|---|
| 600 | 60 | 120 |
| 1500 | 150 | 47 |
| 2300 | 230 | 22 |

The resistance is preferably selected to be rather higher than necessary, in order that it is also possible to use "other" power supply units with a higher charging current without the storage battery being damaged.

The charging logic is an essential constituent part of the charging method as a whole. The configuration according to the invention allows satisfactory charging of the storage battery and differentiated limiting of the operation of the electric toothbrush in different operating states in dependence on the sealing of the inner space. This is described hereinbelow with reference to FIG. 12.

A further advantageous variant provides a holder for the electric toothbrush, e.g. in the form of a stand. The toothbrush plugged into the latter is positioned such that the contact elements are not positioned in the direction in which the water flows or at the drip-off points. It is also intended for the charging operation to be possible when the user does not have the holder to hand. The holder is either purely mechanical, serves only as a supporting and positioning aid for the electric toothbrush and does not contain any electrical components. In the case of this variant, it is to be ensured that the contact elements are freely accessible if the electric toothbrush is placed on the holder. In another variant, the holder contains additional electrical elements, e.g. a timer unit, charging-state display, charging-capacity display, music. These additional electrical elements are supplied by the same contact element as the electric toothbrush itself, i.e. they preferably function at the same operating voltage as the electric toothbrush. In an alternative variant, the holder likewise has an additional storage battery. The holder is only an "intermediate electrical element", which may or may not be used. When traveling, it is likewise possible for the electric toothbrush, in the case of this variant, to be charged directly by the power supply unit. Consequently, the holder has the same plug-in contacts as the power supply unit and the electric toothbrush. In the case of the variants with secondary seals, it is to be ensured that, in addition to the plug-in element of the holder, a corresponding amount of space is provided for the secondary seal, e.g. a recess. The holder preferably contains means which detect the positioning of the electric toothbrush in the holder, or the removal therefrom, in order thus to trigger electrical functions, e.g. timing. The presence of the electric toothbrush is detected by means of a mechanically actuated pushbutton, triggered by the user or as the toothbrush is placed in position. It is likewise possible for the presence of the toothbrush to be detected by an electronic analysis of the charging current/ charging voltage, but this variant involves higher outlay and more cost.

Since considerable plug-in forces are exerted, in particular, in the case of the holder with plug-in contacts, it is proposed to provide the holder with fixing means in relation to the underlying surface. This may be provided by the installation of additional weight or by adhering elements, e.g. a suction cup. If soft material is used for these adhering elements, it is proposed, once again, to use the same soft material which has also already been used for other purposes, e.g. the membrane over pushbuttons, the sealing of electrical components in the inner space, handle hollows for handling purposes, movement of the holder, and to produce these in one operation.

Since the toothbrush only has to be charged up following a number of cleaning cycles, the holder preferably has two set-down positions for the electric toothbrush. One is used for charging purposes (brush is electrically connected) and the other is used purely for setting the toothbrush down, without an electrical connection.

A sales unit contains the electric toothbrush including the power supply unit possibly with, depending on the variant, additional replacement heads/plug-on heads and optionally with the holder. The power supply unit including elements for the power supply connection and the contact elements used for the connection to the electric toothbrush are preferably displayed in a see-through pack, in order that the user can see that the toothbrush is a rechargeable one. As an additional option, it is also possible for the primary or secondary seal to be displayed in the open state, so that the user immediately recognizes how the electric toothbrush can be recharged.

BRIEF DESCRIPTION OF THE DRAWINGS

Examples of the invention are described hereinbelow and illustrated in the drawings, in which, purely schematically:

FIGS. 12*a-h* show circuit diagrams of the charging circuit in various operating states;

FIGS. 14*a* and *b* show a shield for delimiting the cavity;

FIGS. 15*a* and *b* show a closure having an additional switch for producing an alternative switching state;

FIGS. 16*a-h* show basic circuit diagrams for a toothbrush having an additional switch according to FIGS. 15*a* and *b*; and FIG. 17 shows an exemplary razor according to the invention.

DETAILED DESCRIPTION OF EMBODIMENTS

Figure 1:
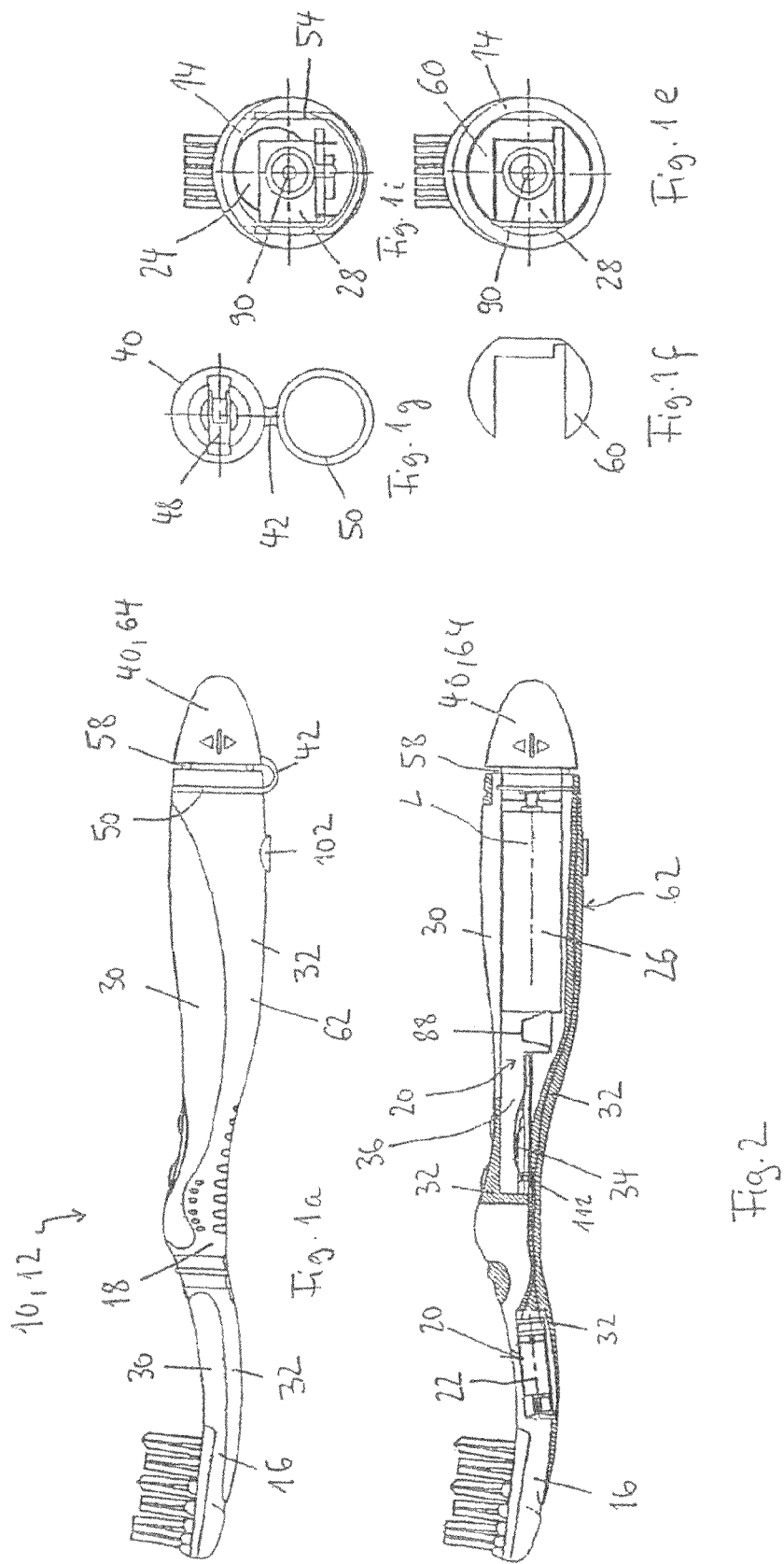
FIGS. 1*a-i* show various views of a toothbrush according to the invention and constituent parts thereof.

FIGS. 1 and 3-10 show various toothbrushes 10 according to the invention, of which the body 12 comprises in each case a bristle-covered head region 16, a handle region 14 and a neck region 18 located therebetween. The head region 16 forms around 5%-20% of the overall length, the neck region 18, which is tapered in relation to the handle region 14, forms around 15%-50% of the overall length, and the handle region forms around 40%-80% of the overall length. A closure 40 is a constituent part of the handle region 14 and, in different variants, can take up 10%-70% of the handle length.

The body 12 contains in each case functional components 20 with an electrically operated functional unit 22, in this case a motor for the vibratory drive (FIGS. 1 and 7-9) or rotary drive (FIGS. 3-6 and 10) of the head region and/or of the bristle plate. The toothbrushes 10 each comprise a rechargeable energy store 24 (storage battery) and a contact element 28. These are fitted on a printed circuit board 38 which is arranged in an inner space 36 of the handle region 13. Also located in the inner space 36 is a switch 34, which merges into a resilient connecting element 88 which, in the installed state, contact-connects a terminal of the energy store 24.

The printed circuit board 38 has means 104 which allow a form-fitting and force-fitting connection to the hard component of the electric toothbrush. In the present case, resilient snap-action noses 104 (FIG. 1*h*) latch in behind a contact bridge 54. The printed circuit 35 board 38 has a thickness of 0.5-3 mm, preferably 1 mm. In a number of variants, the printed circuit board 38 is introduced from behind, with the components mounted thereon, into the inner space 36 of the electric toothbrush 10.

Figure 2:
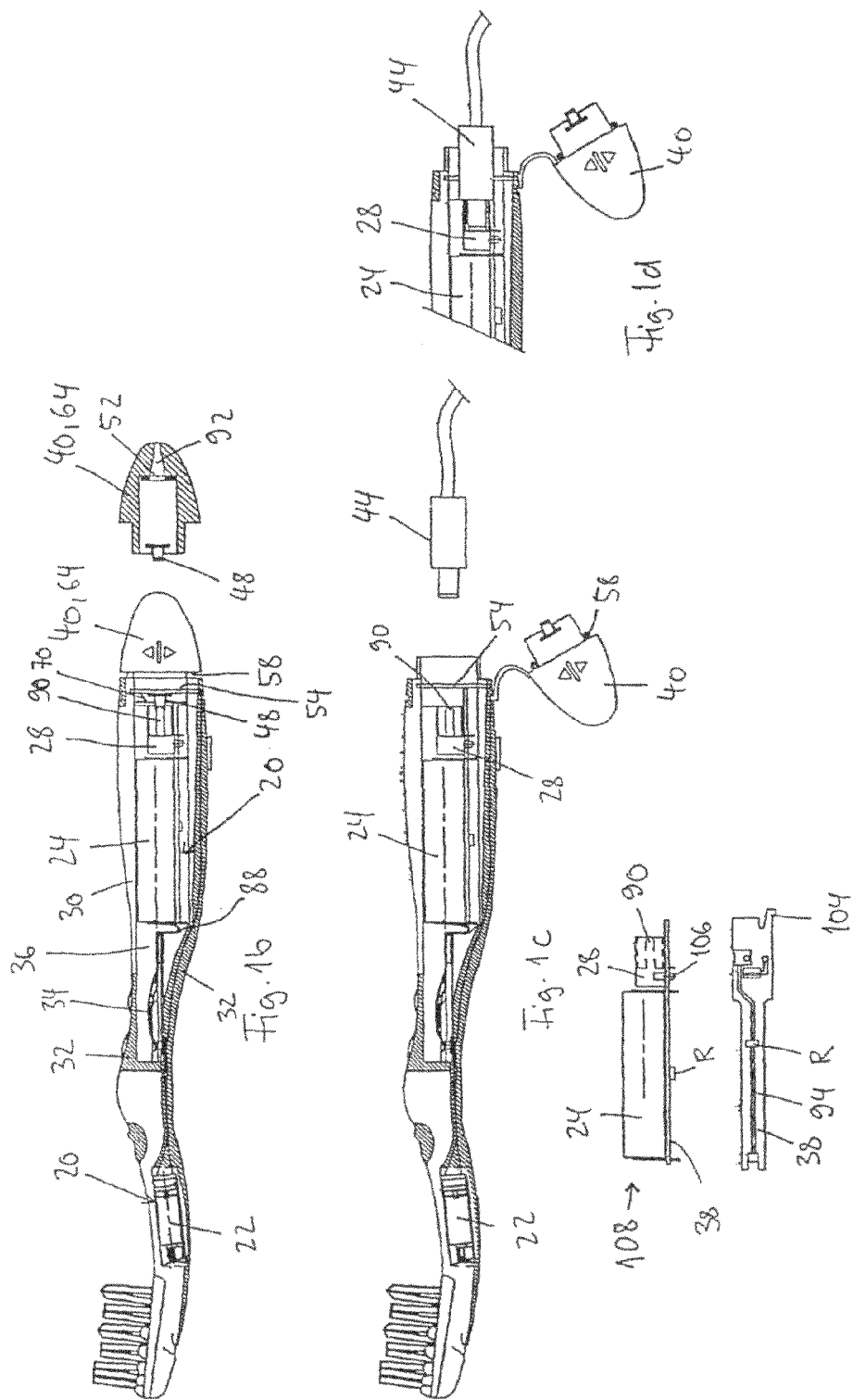
FIG. 2 shows a toothbrush with a conventional, non-rechargeable energy store.
Figure 3:
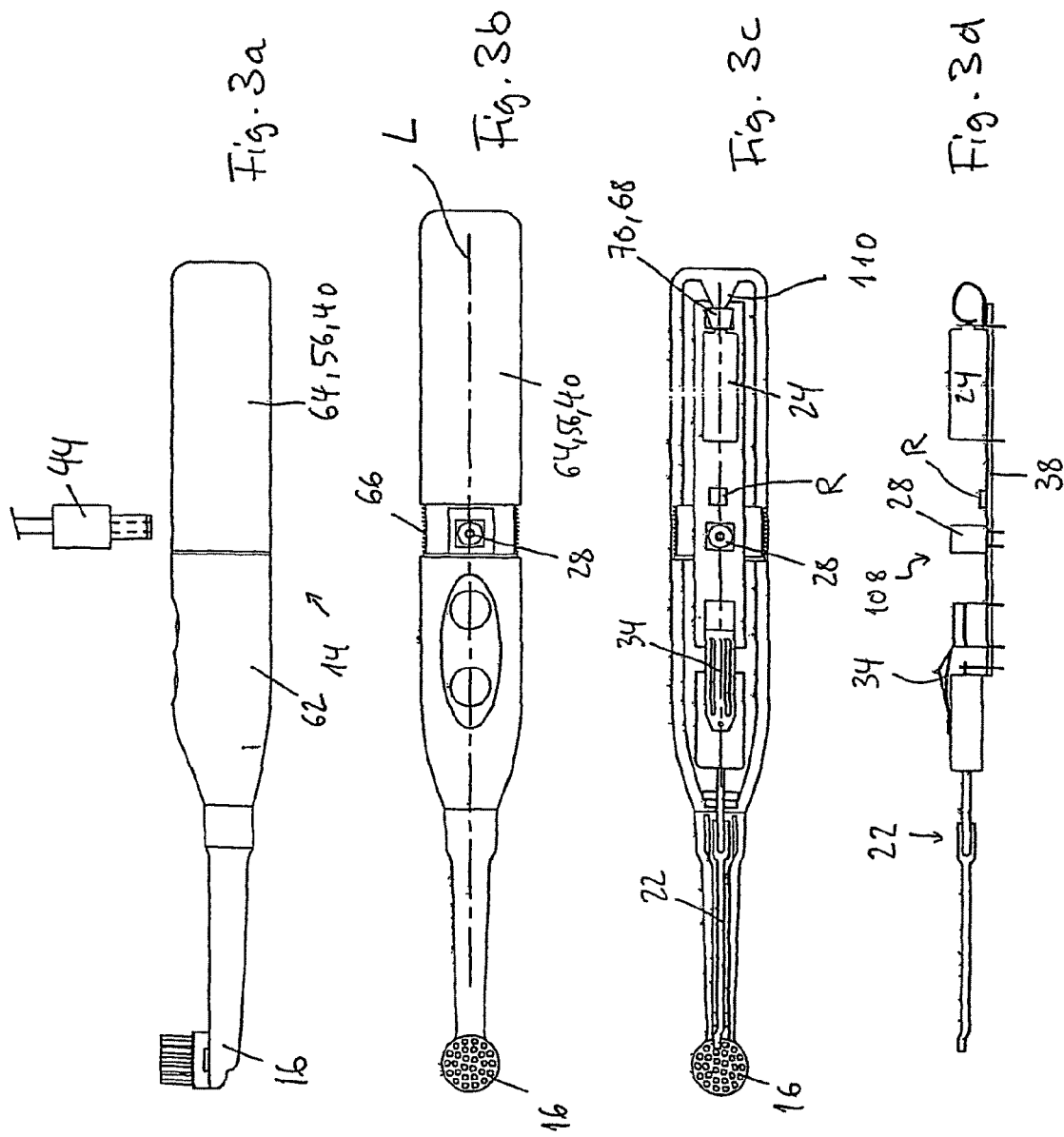
FIGS. 3*a-d*, 4*a-c*, 5*a-c*, 6*a-d*, 7*a*+b, 8, 9, 10 show various views of further toothbrushes according to the invention and constituent parts thereof.
Figure 4:
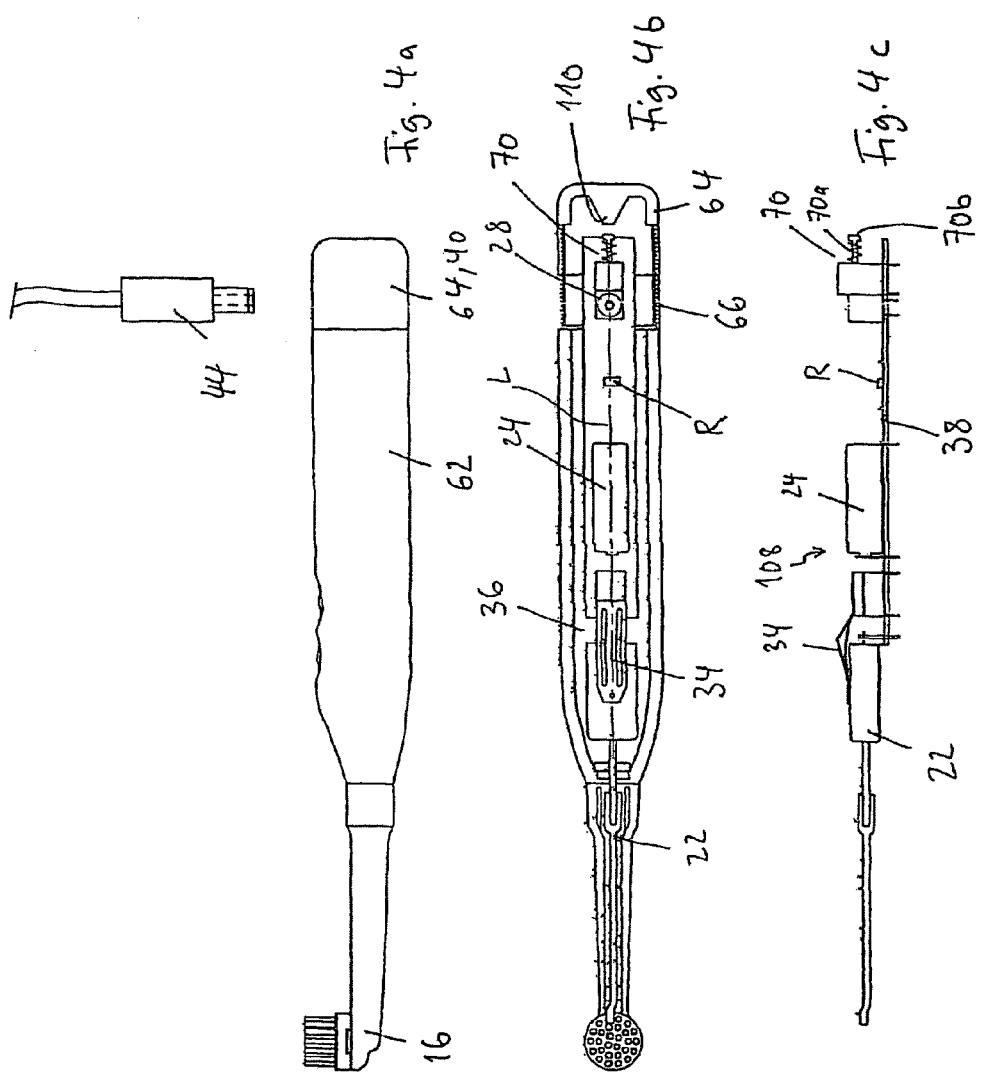
Figure 5:
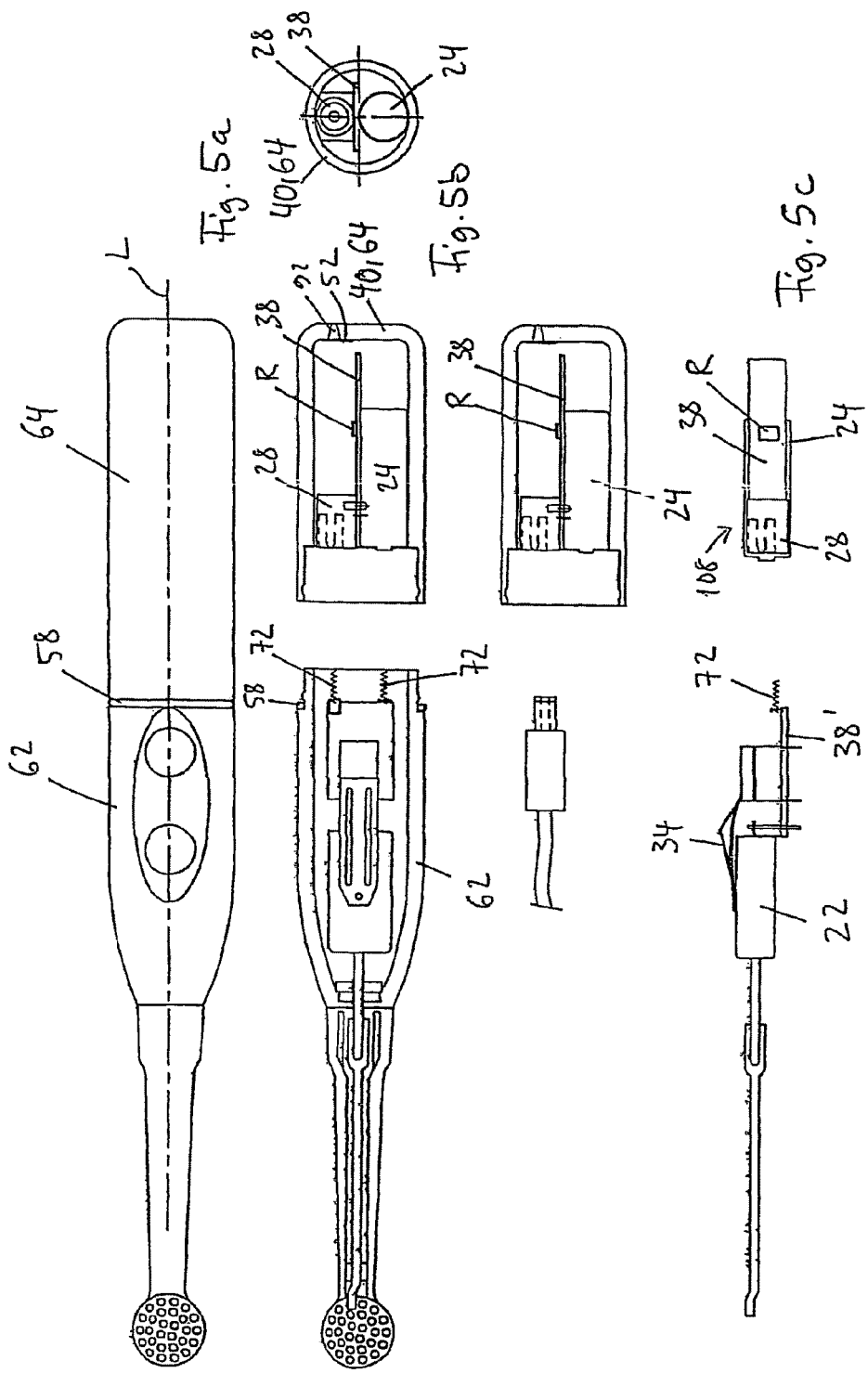
Figure 6:
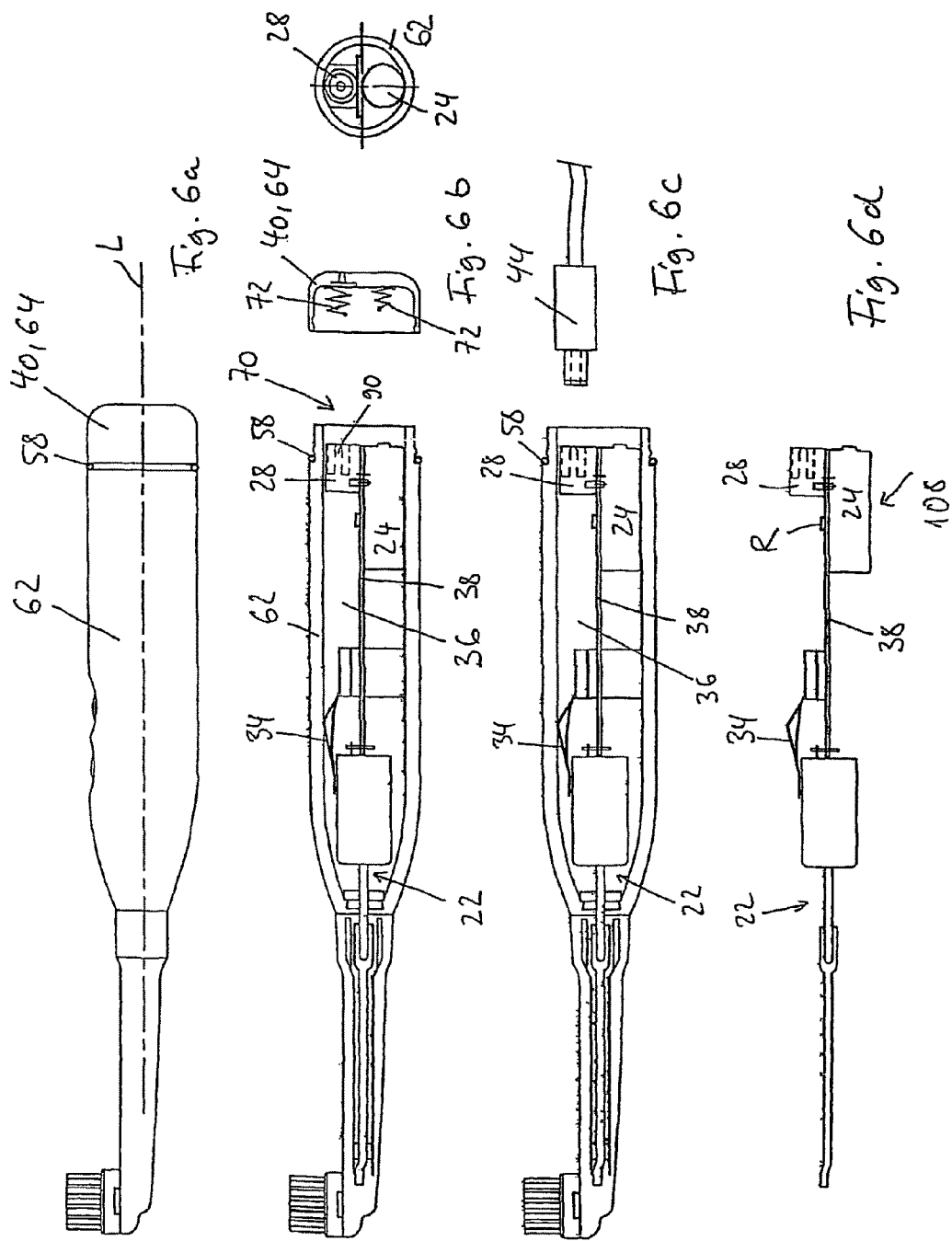
Figure 7:
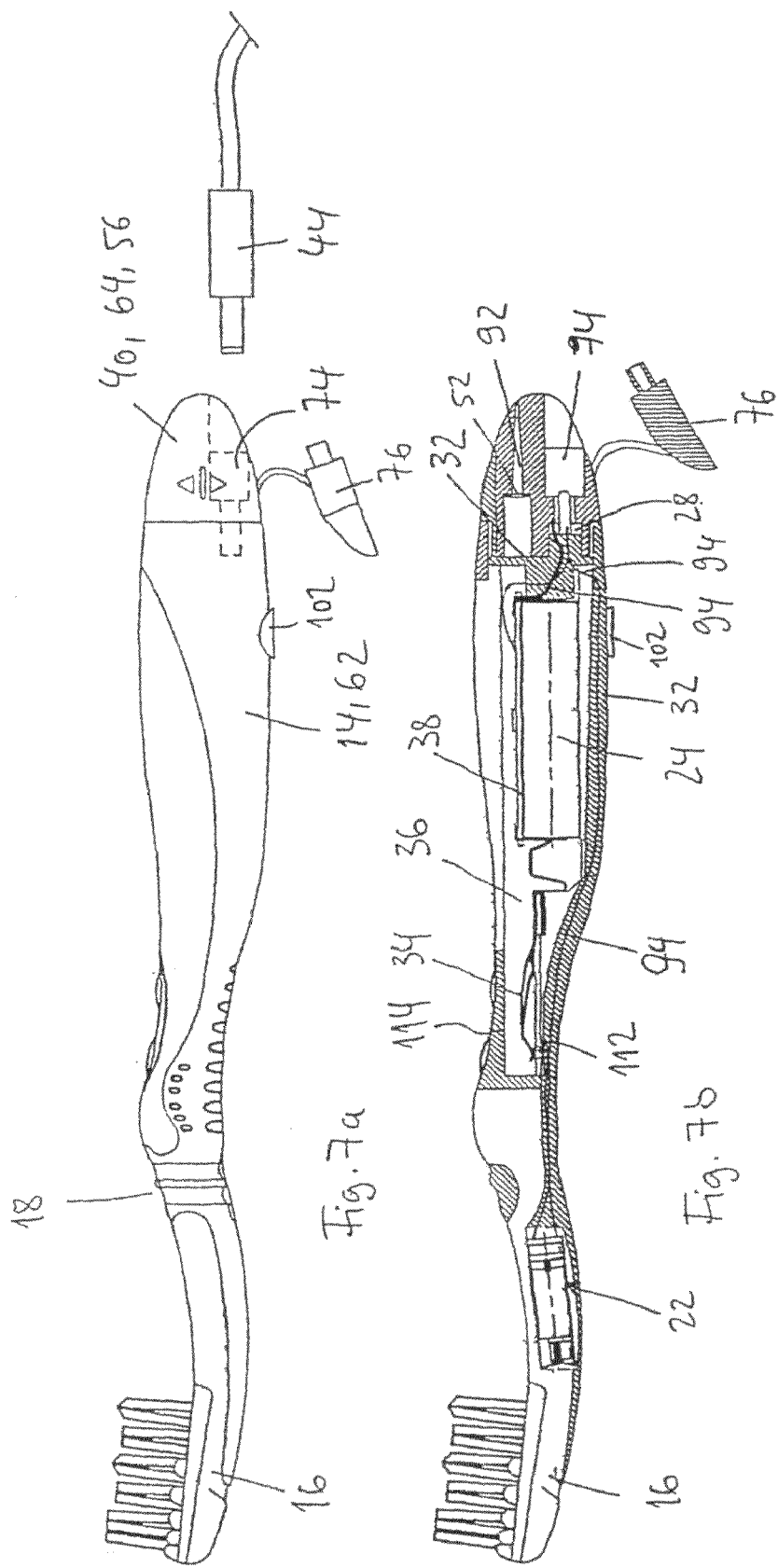

FIG. 2 shows a comparative example of a toothbrush with a non-rechargeable energy store 26 in the form of a battery. The construction and functioning of the toothbrush are described in international patent application PCT/EP03/09681, which was not published before the priority date. The outer configuration of this toothbrush and the installation of the functional unit 22 are realized in a manner identical to the toothbrush which is shown in FIGS. 1*a-c*. It is possible to compensate for the difference in length between the battery 26 and the storage-battery subassembly 108, comprising storage battery 24, contact element 28, printed circuit board 38 and connecting lines (FIG. 1*h*), by resilient connecting elements 88 of different lengths. It is thus advantageously possible to use the same brush body and the same production tools and largely the same production steps. The switch 34 is optionally arranged on the printed circuit board 38 of the storage-battery subassembly 108.

The toothbrush 10 which is shown in FIGS. 1*a-g* is only described hereinbelow to the extent which is necessary for understanding the invention. In respect of construction and production of the body 12 and of the functional components 20, you are referred to PCT/EP03/09681.

The storage battery 24 and contact element 28 in the form of a standard socket are fitted on a printed circuit board 38 (FIG. 1*h*). The contact element 28 is fastened in a form-fitting manner, on the printed circuit board 38 by way of an anchoring element 106. The storage-battery subassembly 108 is pushed into an inner space 36 in a first housing part 62 of the two-part body 12. The inner space 36 is closed by a second housing part 64 in the form of a closure 40 being placed in position. Arranged between the two housing parts is a seal 58, which is integrally molded on the closure 40 or preferably on the hard component 30 of the handle region 14. The seal 58 preferably consists of the same material as the soft component 32 of the body 12, consisting of soft and hard material. The hard component 30 serves for producing the stability-forming constituent parts of the housing, while the soft component 32 serves for producing additional elements, e.g. resilient neck region 18, non-slip coating on the handle region 14, cleaning elements in the head region 16, supporting elements 102 for producing a defined set-down position, for embedding the functional unit 22, and damping elements in the inner space 36 for damping shocks to the storage battery 24. All the elements formed from the soft component are preferably integrally molded in one operation, in particular using the same material.

The closure 40, together with the seal 58, serves as a primary sealing element 56, by means of which the inner space 36, during normal use of the toothbrush, is sealed against the penetration of water and other foreign matter, as is illustrated in FIG. 1*b*. FIGS. 1*c* and 1*d* show the open state, in which the contact element 28 is accessible for a plug 44 of a power supply unit 46 (see FIG. 13). The closure 40 is positioned on the first housing part 62 in the manner of a bayonet, screw-type or snap-action closure and is optionally connected to a fastening ring 50, which is drawn over the first housing part 62, via a film hinge 42 (FIGS. 1*c* and 1*g*). A corresponding recess is provided in the handle part in order to ensure seamless latching in of the fastening ring 50.

As can be seen from the longitudinal-direction view into the inner space in FIG. 1*e*, the inner space 36, in the open state, is only covered by a shield 60 (FIG. 1*f*) which does not have any sealing function. A preferred embodiment of the shield is described below with reference to FIGS. 14*a-e*. The state without the shield 60 is illustrated in FIG. 1*i*. Since it would thus be possible for water to penetrate during the charging operation, the following measures ensure that the functional unit 20 can operate, irrespective of the position of the switch 34, only in the closed, sealed state: as is illustrated in FIGS. 12*a-e*, the manual-actuation switch 34 has connected in series with it a further switch 70, which is formed by a contact strip 48 in the closure 40 in connection with contact bridges 54 in the first housing part 62. The contact strip 48 is illustrated in FIG. 1*g* in the partial view of the closure 40. In the closed state, the contact strip 48 produces an electrically conductive connection between the pin 90 of the contact element 28 and the contact bridges 54, as a result of which the functional unit 22 is basically rendered ready for operation. If the contact element 44 of the power supply unit has been plugged in, the contact bridges 54 are only contact-connected by non-conductive components of the contact element 44, with the result that the switch 70 is open.

A switch 34' can likewise optionally be incorporated in the closure 40. This switch 34' can be used as an alternative to the on/off switch 34 or it can produce an alternative operating state if it is mounted in addition to the switch 34. A closure of this type is described below with reference to FIGS. 15a and b.

The closure 40 contains an opening 92 and a membrane 52, through which the gases produced during operation can escape, but which forms sufficient protection against water.

During the production of the toothbrush, the inner space 36 is formed in the hard component by means of a core and is demolded axially from the rear of the handle part 14. Surfaces, protrusions and recesses are formed here, and these are used for the installation of the switching element 34, of the storage-battery subassembly 108 and of the motor subassembly 22. The storage-battery subassembly 108 is mounted in a flexible manner in the axial direction by means of a spring element 88. Damping elements made of soft material (not illustrated) are preferably provided in the radial direction. The printed circuit board 38 has one or more snap-action elements 104, which once the subassembly has been pushed into a corresponding recess in the hard component, latch in behind one or both legs of the bridge 54. The contact strip 48 and the pin 90 of the socket 28 are arranged such that the contact strip 48 comes into contact with the pin 90 with prestressing when the bayonet closure is rotated. The pin 90 of the socket is preferably located on the axis of rotation of the closure 40.

The closure 40, like the first housing part 62, is produced from a hard or soft component or from a combination thereof. The fastening ring 50 is preferably produced in one operation with the closure and preferably consists of the same material as the rest of the soft constituent parts. It is of flexible and elastic configuration, in order to be able to accommodate the rotation for closing/opening the inner space without any damage. In order that there are no impressions left on the surface of the user's hand during use, the connecting crosspiece 42 between the retaining ring 50 and closure 40 is preferably provided laterally or on the underside of the electric toothbrush.

The storage-battery subassembly has a AAA cell 24. The diameter of the inner space 36, however, is configured such that, instead of this subassembly, it can also accommodate a disposable AA cell 26. The production can thus easily be changed over to a battery-operated toothbrush. In order to bridge the difference in length between a AA cell and a storage-battery subassembly with AAA cell, the contact strip 48 in the closure 40, the switching element 34 or the extension of the latter, designed as spring part 88, is lengthened accordingly. The actual seal 58 of the primary sealing element 56 is soft material or a separate O-ring on the first housing part 62 or on the closure 40.

For production purposes, the following subassemblies are prepared: 1. Motor subassembly 22 with vibration unit, lines, contact pin, contact bridge 54; 2. Closure 40 with degassing membrane 52, contact strip 48, optional retaining ring 50; 3. Storage-battery subassembly 108 with printed circuit board 38 with snap-action element 104, resistor R, storage battery 24, contact element 28, optional shield 60; 4. Switch 34 with spring element 88; 5. Toothbrush head 16 with bristles.

Assembly takes place by way of the following steps:
1. Hard component 30 of the toothbrush;
2. Installing/fixing the motor subassembly 22 on the hard component;
3. Soft component 32 of the toothbrush (overmolding the motor subassembly 22, producing the switching membrane, retaining zones, supporting elements 102, sealing elements, optional soft/resilient cleaning elements, damping elements, flexible zones in the neck region, etc.);
4. Introducing the switching element 34, fixing it on the hard component 30 of the electric toothbrush;
5. Introducing the storage-battery subassembly 108 with shield into the recess of the hard component 30, latching it in behind legs of the contact bridge 54, then optional performance testing;
6. Installing the closure 40 (optionally by means of retaining ring 50);
7. Installing the brush head;
8. Packaging.

FIGS. 3a-d show a further toothbrush according to the invention, having a rotary head and a corresponding drive unit 22. The closure 40, as second housing part 64, takes up a considerable amount of the handle part 14 and accommodates the energy store 24. The contact element 28 is positioned approximately in the center of the handle part 14, in the inner space 36. The first and second housing parts 62, 64 are screwed to one another via a thread 66. The distance by which the closure 40 opens is limited by suitable means. The closure 40 can thus be opened by rotation over a limited distance for the charging operation, complete removal of the closure 40 by the user not being envisaged. The distance corresponds at least approximately to the size of the contact element 28. The contact element 44 of the power supply unit 46 is plugged into the contact element 28, on the front side of the toothbrush, perpendicularly to the longitudinal axis L of the toothbrush 10. As an alternative, it would also be possible to provide a sliding closure which snaps in on the handle part 62.

A switch 70 which is closed automatically when the closure 40 is closed is also provided here. A bent spring part 68 is preferably fitted at the end of the printed circuit board, the spring being forced against a storage-battery terminal by the closure 40 and thus functioning as switch 70. For this purpose, the closure 40 has, on its inside, a protuberance 110 which is arranged on the longitudinal axis L and, in the closed state, presses on the spring part 68 irrespective of the rotary position.

According to the invention, the inner space 36 with the energy store 24 and contact element 28 is closed off in a water-tight manner by a primary sealing element 56 in the form of the second housing part 64, if appropriate with an additional seal (soft material or O-ring).

For production purposes, first of all the following subassemblies are prepared: 1. Motor subassembly 22 with motor, seal, guide; 2. Closure 40 with protuberance 110; 3. Storage-battery subassembly 108 with printed circuit board 38, switch 70, resistor R, storage battery 24, socket 28; 4. Plug-on toothbrush with brush head 16.

The rest of production/assembly takes place by way of the following steps:
1. Hard component 30 of the toothbrush;
2. Soft component 32 of the toothbrush (producing the switching membrane, retaining zones, supporting protuberances, sealing elements, optional soft/resilient cleaning elements, damping elements, flexible zones in the neck region, etc.);

3. Installing/fixing the motor subassembly on the hard component;
4. Introducing the storage-battery subassembly 108 into the recess of the hard component 30 and latching it in, producing an electrical connection here to the motor subassembly by means of plug-in contacts or wires 94;
5. Installing the cover 40;
6. Installing the plug-on toothbrush;
7. Packaging.

FIGS. 4a-c show a similar solution to FIGS. 3a-d. The closure 40 here is considerably shorter and flattened at the end, in order that the toothbrush can be charged in the vertical position. The contact element 28 is located at the rear end of the handle region 14. As an option here, the motor subassembly 22, 34 and the storage-battery subassembly 108 are connected by means of the printed circuit board 38 to form a single subassembly (FIG. 4c) The printed circuit board 38 has a switching element 70, which is closed by means of rotation when the inner space 36 is closed by the closure 40. Two spring parts 70a, 70b are preferably fitted at the closure end of the printed circuit board 38, these spring parts being pressed against one another by the closure 40 and closing the circuit. Production and assembly are analogous to the example from FIGS. 3a-d.

The switch 70 may also be arranged in the closure 40 separately from the contact element 28.

FIGS. 5a-c show an electric toothbrush with a rotating plug-on brush similar to that in FIGS. 3a-d and 4a-c. The contact element 28 and the energy store 24 are located with the printed circuit board 38 in the closure 40, which can be completely removed from the first housing part 62 for charging purposes and is otherwise screwed, plugged or snapped onto the same. In the closed state, two contact springs 72, which are preferably arranged on a further printed circuit board 38' in the first housing part 62, contact-connect a terminal of the storage battery 24 and/or the pin 90 of the contact element 28, which is arranged above the storage battery. These components thus function as switch 70 and, in the closed state, serve for producing a conductive connection between the storage-battery subassembly 108 and the motor subassembly with switch 34.

The storage-battery subassembly, on the printed circuit board 38, has one or more snap-action elements which, once the subassembly has been pushed into a corresponding recess in the hard component of the closure 40, latch in. The storage-battery subassembly preferably has a AA cell. The diameter of the inner space 36 and/or of the corresponding recess in the closure 40, however, is configured such that, instead of this subassembly, it can also accommodate two disposable AA cells. The production can thus easily be changed over to a toothbrush with a disposable battery.

The primary sealing element 56 for closing the inner space 36 is realized by the closure 40, preferably in conjunction with a seal 58, which is arranged in the form of soft material or an O-ring on the electric toothbrush or on the closure 40.

Production/assembly is analogous to the examples which have already been described, with the exception that the storage-battery subassembly is introduced into the recess in the closure and latched in.

FIGS. 6a-d show a modification of the electric toothbrush from FIGS. 5a-c, in the case of which the storage-battery subassembly 108 is located in the handle part of the body 12. The contact element 28 and energy store 24 are likewise arranged one above the other. The closure 40 contains just two spring elements 72, which are connected in a conductive manner to one another. In the closed state of the closure, they short-circuit the pin 90 of the contact element 28 with a storage-battery terminal. In this variant, it is easily possible to change over to operation with a disposable AA battery, since the dimensions of the inner space 36 are sufficient for this purpose. In the case of this closure too, an additional switch 34', as shown in FIGS. 15a and b and described below, could be provided. For this purpose, the spring elements 72 are diverted via the switch 34' analogously to the contact strip 48.

FIGS. 7a and b show an electric toothbrush with a vibration unit 22, a rechargeable energy store 24 and a contact element 28. The basic construction corresponds to FIG. 1. In contrast to the example from FIG. 1, the inner space 36 in the handle region 14 is closed off permanently by a primary seal 56. The primary seal 56 in this case is formed by a second housing part 64 which is in the form of a closure 40, is positioned permanently on the first housing part 62 and, together with the latter, bounds the inner space 36. The closure 40 consists of hard and soft component 30, 32. The contact element 28 and connecting lines 94 from the contact element 28 to the energy store 24 and/or to the printed circuit board 38 are embedded in the soft component 32. The contact element 28 is preferably fixed on the hard component of the closure 40 and overmolded/encapsulated by the soft component. The contact element 28 essentially consists of a hard material (e.g. metal) which withstands the injection pressure and the temperature during overmolding. The closure 40 is permanently connected to the first housing part 62, e.g. by means of welding or a snap-action connection.

The contact element 28 is arranged in a recess 74 which is oriented along the longitudinal axis of the toothbrush 10 and is preferably of a shape which complements the contact element 44 of the power supply unit. The angle of orientation may also be up to +/−90°. An opening 92 with a degassing membrane 52 is likewise arranged in the closure 40.

The switch 70 can be formed by a further switch 34' according to the example shown in FIGS. 15a and b and described further below, so that the switch 72 with attached closure can be actuated.

It is preferred, but not necessary, for the recess 74 to be covered, during normal operation, by a secondary sealing element 76, which can be removed for charging purposes. It is preferably of a shape which complements the recess 74, and it is connected to the actual brush body 12 via a film hinge 42. By virtue of the shape of the secondary sealing element 76, during closure, material which has accumulated in the recess 74 under certain circumstances is displaced.

For production purposes, the following subassemblies are prepared: 1. Motor subassembly 22 with vibration unit, lines, contact pin 112; 2. Closure 40 with degassing membrane 52, contact element 28, possibly connecting lines 94; 3. Storage-battery subassembly 108 with printed circuit board 38, resistor R, storage battery 24, without contact element 28; 4. Switch 34; 5. Toothbrush head 16 with bristles.

Assembly:
1. Hard component of the toothbrush;
2. Installing/fixing the motor subassembly 22 on the hard component;
3. Soft component of the toothbrush (overmolding the motor subassembly, producing the switching membrane 114, retaining zones, supporting protuberances 102, sealing elements, optional soft/resilient cleaning elements, damping elements, flexible zones in the neck region, etc.;
4. Introducing the switching element 34, fixing it on the hard component of the electric toothbrush;
5. Introducing the storage-battery subassembly 108 in the recess of the hard component, then optional 10 performance testing;

6. Producing a conductive connection between the contact element 28 in the closure and the energy store 24;
7. Installing the closure, storage-battery subassembly and motor subassembly;
8. Installing the brush head;
9. Packaging.

Figures 8, 9:
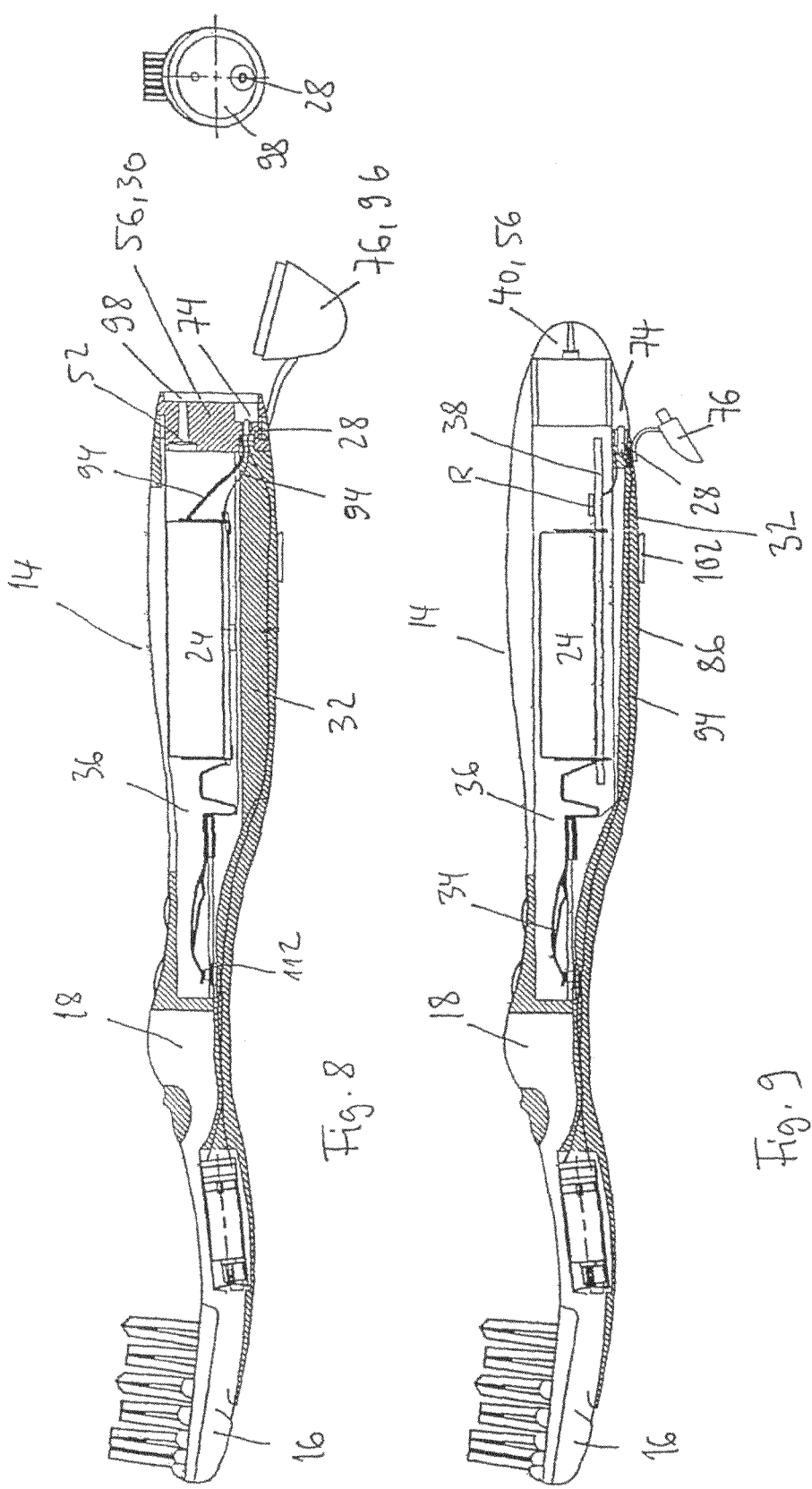
Figure 10:
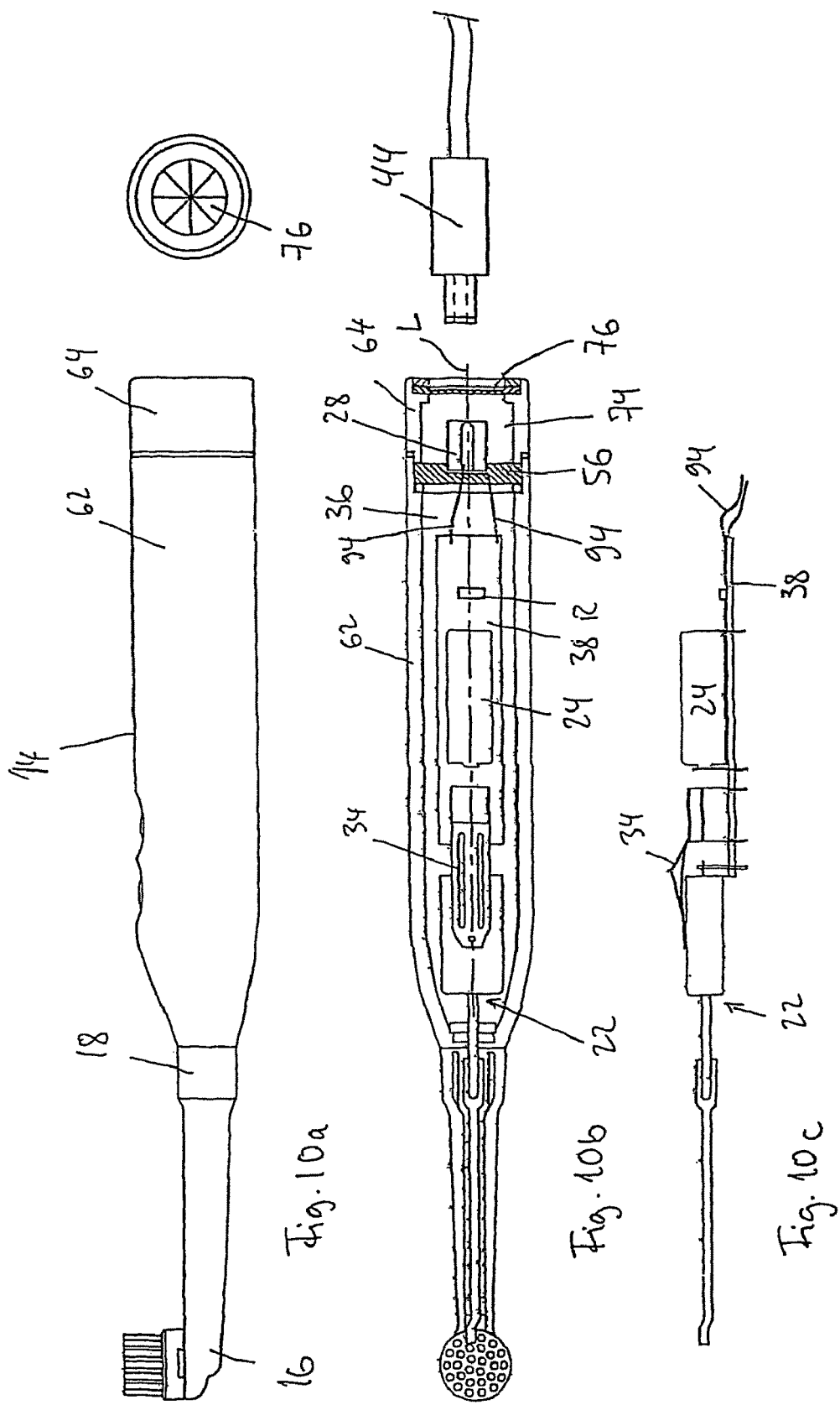

FIG. 8 shows a further example of an electric toothbrush. The contact element 28 is embedded in the handle part 14 and is located on the rear side of the toothbrush, the plug-in direction running longitudinally. The inner space 36 is closed by a primary sealing element 56 made of hard component 30. Connecting lines 94 may be embedded in the soft component 32. A recess 74 for the contact element 44 of the power supply unit and also the degassing opening 92 are arranged in the termination surface 98 on the underside of the toothbrush. The termination surface 98 can be covered by a closure cap 96, which may consist just of hard component. The closure cap 96 functions as a secondary sealing element 76 for protecting the contact element 28 against foreign matter.

The production takes place in a manner analogous to FIGS. 7a and b, with the exception that the contact element 28 is embedded directly in the handle part 14, in particular is encapsulated by soft component 32. This takes place preferably in one operation as the motor subassembly is embedded.

FIG. 9 shows a further example of a toothbrush with a primary sealing element 56 and optional secondary sealing element 76. The recess 74 is located on the rear side 86 of the body 12 and is oriented along the longitudinal axis. The inner space 36 is permanently closed by a closure 40. This functions as primary sealing element 56 and contains a degassing opening 92 with membrane 52. The contact element 28 is located in the wall of the handle part 14 and is optionally covered by the secondary sealing element 76. The contact element 28 is embedded in the soft component 32. The closure 40 may thus consist just of the hard component. This toothbrush is particularly suitable for upright storage, e.g. in a toothbrush glass.

Production takes place in a manner analogous to the example from FIG. 8.

In the case of all the variants, in particular those with a permanently closed inner space 36, it is also possible for the inner space 36 to be filled by a material, provided the contact element 28 remains accessible.

FIGS. 10a-c show a further variant of a toothbrush in which the inner space 36 is permanently closed by a primary sealing element 56. The primary sealing element 56 is formed by a sleeve-like second housing part 64, which is positioned on the first housing part 62 and permanently connected thereto. The second housing part 64 forms a recess 74, in which the contact element 28 is arranged. The second housing part 64, on its side which is directed away from the first housing part 62, is provided with a secondary sealing element 76. This comprises a membrane which is slit in a star-shaped manner and can be pierced by the contact element 44 of the power supply unit, but otherwise provides sufficient protection against water, at least against splash water.

FIG. 10c shows the motor and storage-battery subassembly arranged on a common printed circuit board 38. This subassembly is pushed into the inner space 36 once the hard component has been produced. The contact element is integrated in the separately produced, second housing part 64, in particular it is embedded in the soft component. Before the first and second housing parts 62, 64 are connected, the connecting lines 94 of the storage-battery subassembly and of the contact element 28 are connected.

Figure 11:
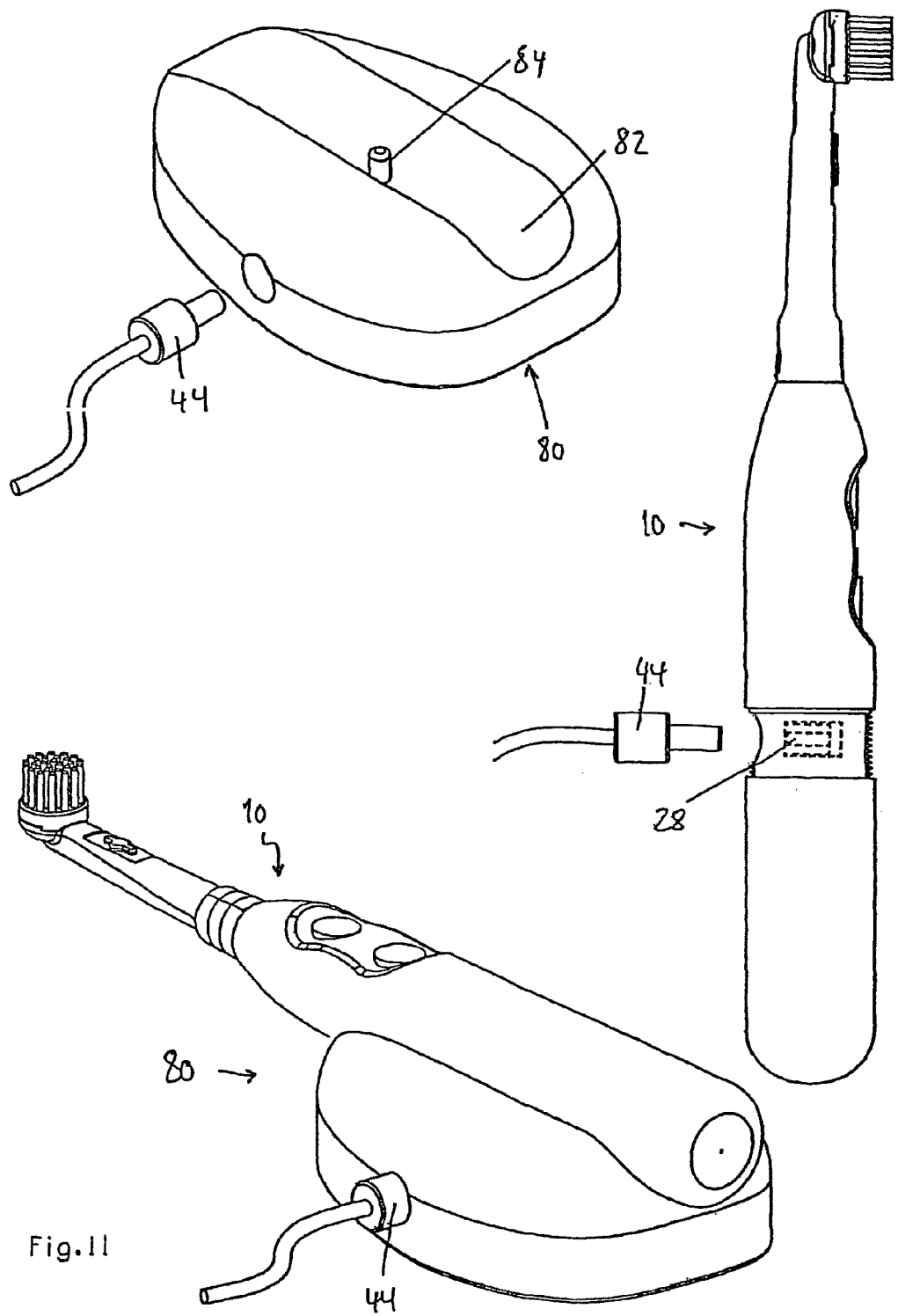
FIG. 11 shows a toothbrush according to the invention with a holder.

FIG. 11 shows a holder 80 for a toothbrush 10 analogous to FIGS. 3a-d. The holder 80 has a hollow 82 adapted to the handle part 14 of the toothbrush 10. The contact element 28 is located on the rear side 86 of the toothbrush 10. When the latter is positioned in the holder 80, it thus comes into contact with a contact element 84 in the hollow. This contact element is galvanically connected to a socket 100, into which the contact element 44 of the power supply unit 46 can be plugged. The toothbrush 10 can be charged via the holder 80 or directly, by virtue of the contact element 44 of the power supply unit 46 being plugged into the contact element 28.

FIGS. 12a-h show circuit diagrams of the charging circuit for the different seal variants.

Case 1: the contact element 28, together with the energy store 24, is located in the inner space 36, which is closed off with sealing action by a closure 40 (FIGS. 1 and 3-5). During normal operation (FIG. 12a), the primary sealing element (closure 40) closes off the inner space 36 in a water-tight manner. A switch 70, which is actuated by placing the closure 40 in position/removing the closure 40, is closed. The user can switch the consumer 22 on and off by a further switch 34. If the closure 40 is removed, the switch 70 inevitably switches off the connection between the storage battery 24 and the consumer 22 (FIG. 12b). In the open, i.e. non-sealed state, it is thus no longer possible for the electric toothbrush to be switched on. During charging of the storage battery 24 by virtue of the plug 44 being plugged into the socket 28, the inner space 36 is open (FIG. 12c). By providing the switch 70, it is then additionally possible to achieve the situation where charging of the storage battery 24 can always take place, irrespective of the state of the switch 34, only if the consumer 22 is not operating. This is because, if the consumer 22 was operating (i.e. 34 and 70 closed) during charging of the storage battery 24 and the storage battery 24 was completely emptied, charging would not be possible.

Case 2 (FIGS. 12d-e): the inner space 36 is completely sealed in relation to the contact element 28 in each operating state (FIGS. 7-10). Since the primary seal is not removed, a distinction is only made between two operating states, to be precise the normal operating state (FIG. 12d) and the charging state (FIG. 12e). The operation of opening or closing the secondary seal need not, in fact, have any influence on the charging circuit. For the purpose of charging the storage battery 24, the socket 28 preferably has an integrated switch 70 which performs the task of the switch 70 actuated by the closure in case 1. This integrated switch 70 guarantees that the storage battery 24 can be charged irrespective of the switching state of the switch 34. The integrated switch 70 is opened when the plug 44 is plugged in (FIG. 12e), and thus prevents the situation where a completely empty storage battery 24 cannot be charged because the consumer 22 is connected to the storage battery 24 via the switch 34.

If, with the inclusion of this potential disadvantage, the integrated switch 70 is not provided, operation with the plug 44 plugged in is conceivable in principle.

Case 3 (FIGS. 12f-h): in a manner analogous to case 1, a distinction is made here, once again, between three operating states. The switch 70 corresponds to the spring element 72 shown in FIG. 6, and the switch 70', as in case 2, is preferably integrated in the contact element 28.

FIG. 12f describes the normal operating state. The user switches the consumer 22 on and off via the switch 34. The switches 70 (actuated by the closure) and 70' (integrated in the contact element 28) are closed. The resistor R is short-circuited by the closed switch 70.

FIG. 12g describes the state in which the closure has been removed and the consumer, irrespective of the state of the switch 34, on account of the risk of contamination, is not to function. In this operating state, it is indeed the case that the consumer 22 is in electrical connection with the storage battery 24 via the resistor R, but it will nevertheless not be possible to switch it on, since the resistance of the resistor R is selected to be higher than the internal resistance of the consumer 22, the aim likewise being achieved as a result.

FIG. 12h proposes an additional switch 70' preferably integrated in the contact element 28. If the plug 44 is plugged in (and the switch 70' is thus opened), it is thus possible, as in case 2, to prevent the situation where a completely emptied storage battery 24 cannot be charged because the consumer 22 is connected to the power supply unit 46 via the switch 34.

If, with the inclusion of this potential disadvantage, the integrated switch 70' is not provided, operation with the plug 44 plugged in, as in case 2, is likewise conceivable in principle.

Figure 13:
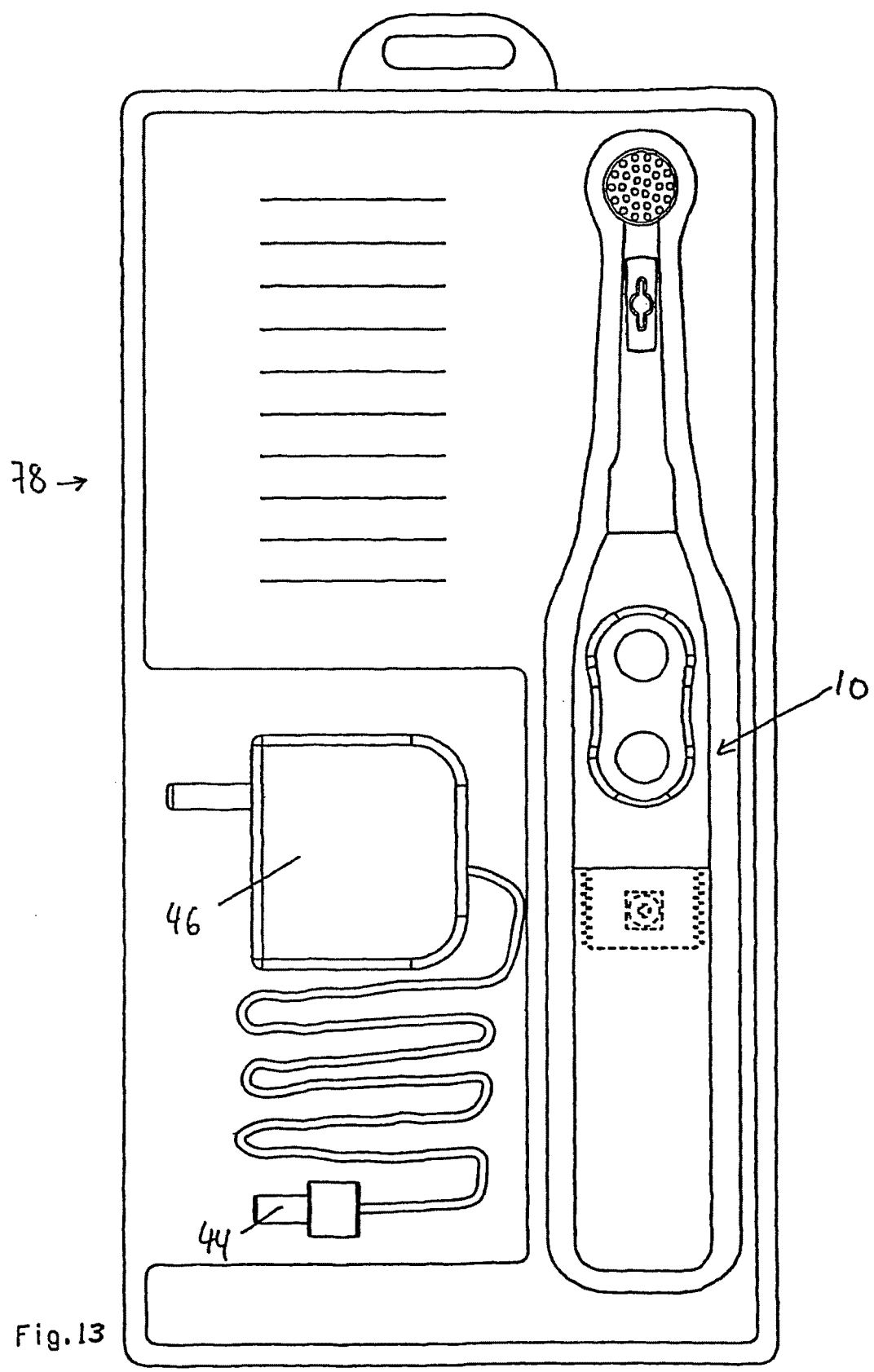
FIG. 13 shows a sales unit with a toothbrush according to the invention and a power supply unit.

FIG. 13 shows a sales set 78 in which a toothbrush 10 and power supply unit 46 are displayed in a see-through pack.

FIGS. 14a and b show a design variant of the shield 60 which has already been sketched in FIG. 1f in a view in the direction of the toothbrush axis. The shield 60 comprises a body 138 which surrounds a cutout 140 which is open on one side and in the direction of the toothbrush axis. The contact element is inserted into this cutout 140 during use. In this case, a latching lug 142 latches in behind the contact element. The shield is secured to the storage-battery subassembly in this way. Furthermore, securing means 144 are arranged on the outer wall of the body 138 and can be used to secure the shield 60 on the toothbrush handle, so that the storage-battery subassembly is prevented from falling out. These securing means 144 are formed, for example, by projections which latch into the hard component of the toothbrush handle. In this case, soft material may be displaced by the projections. FIGS. 15a and b show views of a closure 40 having a switch 34' which can be used as an alternative or in addition to the on/off switch 34 described above. The switch 34' has two switching positions, for example. In a first switching position, the pin 90 and the contact bridge 54 are short-circuited by means of the switch 34', this corresponding to the normal operating state. In the other switching position, the connection between the pin 90 and the contact bridge 54 can be diverted into a further electrical component 124 which produces an alternative operating state. For example, the electrical component may, for example by means of a Schottky diode, reduce the voltage and thus correspondingly reduce the motor speed or power. This alternative closure may of course also be used in an electric toothbrush operated by a non-rechargeable battery. In this case, contact is made with a battery pole rather than with the pin 90.

The closure has the following components: the contact strip 48 contact-connects only the contact bridge 54, but not the pin 90 as in the original variant. Two electrical connecting lines 120, 122 are routed from the contact strip 48 to the switch 34' which is arranged in the closure 40. A first electrical connection 120 passes directly to the switch 34' (short circuit), and a second electrical connection 122 is routed via the electrical component 124 which changes the operating state. As a function of the switch position, the electrical circuit is closed directly or via the electrical component, so that an alternative switching state which is influenced by the component can be produced. An electrical connection, which is preferably only conductive in the closed state and is realized here by a stud 126 with a spring 128, is routed from the switch 34' back to the pin 90 through a recess 130 in the contact strip 48.

If the switch 34' is used as a primary (on/off) switch, only the first electrical connection 120 to the contact strip 48 is used to produce the on/off switching state; 5 the other electrical connection 122 is not used.

The closure is preferably produced in two parts. All of the electrical components are fitted to an inner, cylindrical first part 132 comprising a hard component. A sleeve-like second part 134 consists of a hard-component ring which surrounds the cylindrical first part 132, and a preferably soft-component switching membrane 136 which allows the switch 34' to be pressed. The soft component is preferably transparent, in order to make the switch and the switching state visible. The two closure parts 132, 134 are then preferably permanently connected to one another, for example by snap-action, welding or gluing.

The outer sleeve 134 may have a hole which is covered by a ventilation membrane. The ventilation membrane is preferably fixed by being clamping in with the aid of the inner sleeve 132 and/or by being adhesive bonded.

The closure shown in FIGS. 15a and b can also be used in slightly modified form for the other refinement variants. The closure can likewise also be used in another context than with a rechargeable toothbrush, for example in a toothbrush with a battery, and also in other electrically operated personal-care devices, such as shavers. For example, FIG. 17 shows an alternative exemplary personal-care device in which the toothbrush head 16 of FIG. 17 has been substituted with a razor head 16'. Other like-numbered elements remain the same.

FIGS. 16a-h show basic circuit diagrams for the variant with an additional switch 34' described above with reference to FIGS. 15a and b. The circuit diagrams correspond in principle to FIGS. 12a-h, with the difference that the on/off switch 70 (realized by the closure) in that figure has been replaced by a switch subassembly 146 with a switch 34' which can assume two switching states. The switch subassembly 146 is integrated in the closure 40 of the toothbrush. The state in which the closure is removed is illustrated in FIGS. 16b, 16c, 16e, 16g and 16h. Only the differences from FIGS. 12a-h are described below, otherwise reference is made to the explanations for FIGS. 12a-h.

The switch subassembly 146 has two lines 120, 122 which are connected in parallel and of which one is routed via an electrical component 124, a Schottky diode in this case. The electrical circuit can be closed by the switch 34' either via the short-circuit line 120 or via the component 124, provided that the closure 40 is fitted to the toothbrush body. If the closure 40 is removed, the switch 34' does not operate. The functions described above with reference to FIGS. 12a-h are produced via the short-circuit line 120. An additional switching state is realized via the electrical component 124.

What is claimed is:
1. A toothbrush comprising:
   a body including a handle region, a head region and a neck region located between the handle region and the head region, the body comprising a first housing part, a second housing part and an inner space, the handle region being formed by the first and/or second housing part, the first and second housing parts being movable relative to one another between an open position and a closed position,
   functional components which are arranged, at least in part, within the body and comprise an electrically operated functional unit, an electric energy store and at least one contact element, the at least one contact element being formed to produce an electrically conductive connection to a corresponding further contact element located outside the body, and sealing means for sealing the inner space at least against splash water when the first and second housing parts are in the closed position, wherein:

the energy store and the at least one contact element are arranged in the inner space of the body and the inner space is closable and openable at least to the extent where the at least one contact element is accessible for the corresponding further contact element from the outside when the first and second housing parts are in the open position, and the first and second housing parts are connected to one another by screw or bayonet means.

2. The toothbrush as claimed in claim 1, wherein the second housing part is a closure which closes off the inner space.

3. The toothbrush as claimed in claim 1, wherein one of the first and/or second housing part is displaceable along a longitudinal axis of the body.

4. The toothbrush as claimed in claim 1, wherein the screw means comprise a thread with a distance-limiting means.

5. The toothbrush according to claim 1, wherein the contact element and the energy store are arranged at a carrier unit forming an energy store subassembly.

6. The toothbrush according to claim 5, wherein the energy store subassembly has the size of a conventional battery.

7. The toothbrush according to claim 5, further comprising snap-action means for connecting the carrier unit to the body.

8. The toothbrush according to claim 1, wherein the first housing part is permanently connected to the second housing part.

9. The toothbrush according to claim 1, further comprising a shield arranged in a region of the contact element to shield the functional components, with the exception of the contact element, against splash water in the open position of the first and second housing parts.

10. The toothbrush according to claim 1, wherein the contact element is oriented such that the electrically conductive connection to a corresponding further contact element located outside the body is oriented in the longitudinal direction of the toothbrush.

11. The toothbrush according to claim 1, wherein the contact element is oriented such that the electrically conductive connection to a corresponding further contact element located outside the body is oriented perpendicular to the longitudinal direction of the toothbrush.

12. The toothbrush according to claim 1, wherein the functional unit is deactivated when the contact element and the further contact element are in a conductive connection.

13. The toothbrush according to claim 1, comprising at least one structure-forming hard component and at least one soft component.

14. The toothbrush according to claim 13, wherein the at least one hard component is chosen from the group consisting of polystyrene, acrylonitrile-butadiene-styrene, styrene-acrylonitrile, polyester, polyamide, and polypropylene, and the at least one soft component is a thermoplastic elastomer.

15. The toothbrush according to claim 1, comprising a separating plane defined between the first and second housing part, the contact element being arranged in the immediate vicinity of the separating plane.

16. The toothbrush according to claim 1, wherein the electrically operated functional unit is a vibration device that causes the brush head to vibrate.

17. The toothbrush according to claim 1, wherein the electrically operated functional unit is a drive that oscillates the head part.

18. The toothbrush according to claim 1, wherein the electrically operated functional unit is a music or light emitting device.

19. A sales unit comprising a toothbrush as claimed in claim 1, wherein the toothbrush is arranged in a pack with the at least one contact element of the toothbrush visible from outside the pack.

20. A sales unit comprising a toothbrush as claimed in claim 1, wherein the toothbrush is arranged in a pack in which the sealing means is displayed in the open state.

21. A toothbrush comprising:

body including a handle region, a head region and a neck region located between the handle region and the head region, the body comprising a first housing part, a second housing part and an inner space, the handle region being formed by the first and/or second housing part, the first and second housing parts being movable relative to one another between an open position and a closed position, functional components which are arranged, at least in part, within the body and comprise an electrically operated functional unit, an electric energy store and at least one contact element, the at least one contact element being formed to produce an electrically conductive connection to a corresponding further contact element located outside the body, switching means interacting with one of the first and second housing parts to deactivate the functional unit when the first and second housing parts are in the open position, and sealing means for sealing the inner space at least against splash water when the first and second housing parts are in the closed position, wherein:

the energy store and the at least one contact element are arranged in the inner space of the body and the inner space is closable and openable at least to the extent where the at least one contact element is accessible for the corresponding further contact element from the outside when the first and second housing parts are in the open position.

22. The toothbrush as claimed in claim 21, wherein the switch comprises the contact element and a part which is movable relative to the contact element, the part being connected in an electrically conductive manner to the contact element in the closed position of the first and second housing parts.

23. The toothbrush as claimed in claim 21, wherein the second housing part is a closure which closes off the inner space.

24. The toothbrush as claimed in claim 21, wherein one of the first and/or second housing part is displaceable along a longitudinal axis of the body.

25. The toothbrush according to claim 21, wherein the contact element and the energy store are arranged at a carrier unit forming an energy store subassembly.

26. The toothbrush according to claim 25, wherein the energy store subassembly has the size of a conventional battery.

27. The toothbrush according to claim 25, further comprising snap-action means for connecting the carrier unit to the body.

28. The toothbrush according to claim 21, wherein the first housing part is permanently connected to the second housing part.

29. The toothbrush according to claim 21, further comprising a shield arranged in a region of the contact element to shield the functional components, with the exception of the contact element, against splash water in the open position of the first and second housing parts.

30. The toothbrush according to claim 21, wherein the contact element is oriented such that the electrically conductive connection to a corresponding further contact element located outside the body is oriented in the longitudinal direction of the toothbrush.

31. The toothbrush according to claim 21, wherein the contact element is oriented such that the electrically conductive connection to a corresponding further contact element located outside the body is oriented perpendicular to the longitudinal direction of the toothbrush.

32. The toothbrush according to claim 21, wherein the functional unit is deactivated when the contact element and the further contact element are in a conductive connection.

33. The toothbrush according to claim 21, comprising at least one structure-forming hard component and at least one soft component.

34. The toothbrush according to claim 33, wherein the at least one hard component is chosen from the group consisting of polystyrene, acrylonitrile-butadiene-styrene, styrene-acrylonitrile, polyester, polyamide, and polypropylene, and the at least one soft component is a thermoplastic elastomer.

35. The toothbrush according to claim 21, comprising a separating plane defined between the first and second housing part, the contact element being arranged in the immediate vicinity of the separating plane.

36. The toothbrush according to claim 21, wherein the electrically operated functional unit is a vibration device that causes the brush head to vibrate.

37. The toothbrush according to claim 21, wherein the electrically operated functional unit is a drive that oscillates the head part.

38. The toothbrush according to claim 21, wherein the electrically operated functional unit is a music or light emitting device.

39. A sales unit comprising a toothbrush as claimed in claim 21, wherein the toothbrush is arranged in a pack with the at least one contact element of the toothbrush visible from outside the pack.

40. A sales unit comprising a toothbrush as claimed in claim 21, wherein the toothbrush is arranged in a pack in which the sealing means is displayed in the open state.

41. An electrically operated personal-care device having a body defining a handle region and a head region and having functional components that are arranged, at least in part, within the body and comprise an electrically operated functional unit and an electrical supply device for the functional unit, the electrical supply device having an energy store, the body comprising a first housing part and a second housing part, the second housing part forming a closure and being connectable to the first housing part, the first and second housing part enclosing an inner space that houses the energy store, wherein the closure comprises a switch for switching the functional unit on or off, an inner, cylindrical first part comprising a hard plastic component and all of the electrical components of the closure, a sleeve-like second part consisting of a hard plastic component ring which surrounds the cylindrical first part, and a soft plastic component switching membrane integrally molded with the closure which allows the switch to be pressed, wherein the first part and the second part of the closure are permanently connected to one another by snap-action, welding or gluing.

42. An electrically operated personal-care device having a body defining a handle region and a head region, and having functional components that are arranged, at least in part, within the body and comprise an electrically operated functional unit and an electrical supply device for the functional unit, the electrical supply device having or being connectable to an energy store, the body comprising a first housing part containing the electrically operated functional unit and a second housing part forming a closure and connectable to the first housing part, the first and the second housing parts enclosing an inner space for housing the energy store, whereby an electrically conductive connection between the functional unit and the electrical supply device is interrupted in an open state of the closure, the device further including a primary on/off switching element located in the first housing part and switching the electrically operated functional unit between ON and OFF states and a secondary on/off switching element located in the second housing part and serving to activate an alternative operating state of the functional unit by a change of a voltage.

43. The personal-care device according to claim 42, further comprising a Schottky diode for producing the alternative operating state.

44. A toothbrush comprising:
a body including a handle region, a head region and a neck region located between the handle region and the head region, the body comprising a first housing part, a second housing part and an inner space, the handle region being formed by the first and/or second housing part, the first and second housing parts being movable relative to one another between an open position and a closed position, functional components which are arranged, at least in part, within the body and comprise an electrically operated functional unit, an electric energy store and at least one contact element, the at least one contact element being formed to produce an electrically conductive connection to a corresponding further contact element located outside the body, switching means interacting with the second housing part to deactivate the functional unit when the first and second housing parts are in the open position, and sealing means for sealing the inner space at least against splash water when the first and second housing parts are in the closed position, wherein:

the energy store and the at least one contact element are arranged in the inner space of the body and the inner space is closable and openable at least to the extent where the at least one contact element is accessible for the corresponding further contact element from the outside when the first and second housing parts are in the open position.

\* \* \* \* \*